US006436638B1

(12) United States Patent
De Leon et al.

(10) Patent No.: US 6,436,638 B1
(45) Date of Patent: *Aug. 20, 2002

(54) CRYPTOSPORIDIUM DETECTION METHOD

(75) Inventors: Ricardo De Leon, Irvine; Paul A. Rochelle, Manhattan Beach, both of CA (US)

(73) Assignee: Metropolitan Water District of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/326,074

(22) Filed: Jun. 4, 1999

Related U.S. Application Data

(63) Continuation-in-part of application No. 09/100,649, filed on Jun. 8, 1998, now abandoned, which is a continuation of application No. 08/647,351, filed on May 9, 1996, now Pat. No. 5,770,368, which is a continuation-in-part of application No. PCT/US97/07972, filed on May 8, 1997.

(51) Int. Cl.$^7$ .......................... C12Q 1/68; C12N 15/10; C12N 15/30

(52) U.S. Cl. .......................... 435/6; 435/325; 435/91.1; 435/91.2; 435/7.21; 435/7.22; 435/91.4; 435/91.5; 435/91.51; 536/23.1; 536/24.3; 536/24.31; 536/24.32; 536/24.33

(58) Field of Search .......................... 435/326, 6, 91.1, 435/91.2, 7.21, 7.22, 91.4, 91.5, 91.51; 536/23.1, 24.3, 24.31, 24.32, 24.33

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 4,801,530 A | 1/1989 | Noguiera et al. |
| 4,908,308 A | 3/1990 | Van der Ploeg et al. |
| 4,957,858 A | 9/1990 | Chu et al. |
| 4,965,188 A | 10/1990 | Mullis et al. |
| 4,983,511 A | 1/1991 | Geiger et al. |
| 5,004,682 A | 4/1991 | Roberts et al. |
| 5,035,996 A | 7/1991 | Hartley |
| 5,250,411 A | 10/1993 | Ayyanathan et al. |
| 5,298,392 A | 3/1994 | Atlas et al. |
| 5,409,818 A | 4/1995 | Davey et al. |
| 5,418,149 A | 5/1995 | Gelfand et al. |
| 5,437,990 A | 8/1995 | Burg et al. |
| 5,770,368 A | 6/1998 | De Leon et al. |
| 5,807,670 A * | 9/1998 | Muerhoff et al. ............. 435/5 |

FOREIGN PATENT DOCUMENTS

| | | |
|---|---|---|
| WO | WO8909835 | 10/1989 |
| WO | WO9006995 | 6/1990 |

OTHER PUBLICATIONS

Gerald J. Nuovo et al, Detection of Human Papillomavirus DNA in Formalin–fixed Tissues by In Situ Hybridization After Amplification by Polymerase Chain Reaction, American Journal of Pathology, vol. 139, No. 4, Oct. 1991.*

Abbaszadegan, M.,et al, "Detection of viable Giardia cysts in water samples using polymerase chain reaction," Proceedings American Water Works Association, Water Quality Technology Conference, Toronto (1993).

Aggarwal, A. et al., "Conserved Sequences of the HSP Gene Family in *Giardia lamblia*," In: *Advances in Giardia Research* 173–175 (1988), Ed. P. M. Wallis & B.R. Hammond, University of Calgary Press, Calgary.

Aggarwal, Anita et al., A heat shock protein gene in *Giardia lamblia* unrelated to HSP70, *Nucleic Acids Research*, 18(11):3409 (1990).

Awad–El–Kariem, et al., "Detection and species identification of Cryptosporidium oocysts using a system based on PCR and endonuclease restriction," *Transactions of the Royal Society of Tropical Medicine and Hygiene* 88:19–22 (1994).

Barany, F. "Genetic Disease Detection and DNA Amplification Using Cloned Thermostable Ligase," *Proc. Natl. Acad. Sci. USA,* 88:189–193 (1991).

Cai et al., PCR cloning and nucleotide sequence determination of the 18s rRNA genes and internal transcribed spacer 1 of the protozoan parasite *Cryptosporidium muris, Biochim. Biophys. Acta,* 1131:317–320 (1992).

Chrisp et al., "Similarities and differences between DNA of *Cryptosporidium parvum* and *C. wrairi* detected by the polymerase chain reaction," *Folia Parasitol,* 41:97–100 (1994).

Duck, G. et al., "Probe Amplified System Based on Chimeric Cycling Oligonucleotides," *Biotechniques,* 9:142–147, (1990).

(List continued on next page.)

Primary Examiner—David Guzo
(74) Attorney, Agent, or Firm—David A. Farah; James W. Collett; Sheldon & Mak

(57) ABSTRACT

A method for selectively detecting the presence of *C. parvum* organisms in a sample. A method for selectively detecting the presence of *C. parvum* organisms and for detecting the presence of *G. lamblia* organisms, simultaneously, in a sample. A method for selectively detecting viable *C. parvum* organisms in a sample potentially containing viable *C. parvum* organisms. A method for selectively detecting viable *C. parvum* organisms and for detecting viable *G. lamblia* organisms, simultaneously. A method for selectively detecting infectious *C. parvum* organisms in a sample, and in another embodiment, additionally comprising detecting viable *G. lamblia* organisms in the sample, simultaneously. Kit for use in performing these methods.

29 Claims, 11 Drawing Sheets

OTHER PUBLICATIONS

DuPont, H.L., et al., "The Infectivity of *Cryptosporidium parvum* in Healthy Volunteers," *New England Journal of Medicine*, 332(13):855–9 (1995).

Eddy, R.J. et al., "Aginactin, an Agonist–regulated F–actin Capping Activity Is Associated with an Hsc70 in Dictyostelium," *The Journal of Biological Chemistry*, 268(13):23267–23274 (1993).

Favennec, L., et al., "Adherence and multiplication of Giardia intestinalis on human enterocyte–like differentiated (CaCo–2) cells in vitro," *Parasitology Research*, 76:581–4 (1990).

Filkorn, R., et al. "Selective Detection of Viable Cryptosporidium Oocysts by PCR," *Zentralblatt Hyg. & Umweltmed* 195:489–494 (1994).

Gooze et al., Amplification of a *Cryptosporidium parvum* Gene Fragment Encoding Thymidylate Synthase, *J. 0Protozool* 38(6):56S–58S (1991).

Guatelli, J.C. et al., "Isothermal, In Vitro Amplification of Nucleic Acids by a Multienzyme Reaction Modeled After Retroviral Replication," *Proc. Natl. Acad. Sci. USA*, 87:1874–1878 (1990).

Gupta et al., "Cloning of *Giardia lamblia* heat shock protein HSP 70 homologs: implications regarding origin of eukaryotic cells and of endoplasmic reticulum," *Proc. Natl. Acad. Sci. USA* 91:2895–2899 (1994).

Haus, Ulrike, et al., "The heat shock cognate protein from Dictyostelium affects actin polymerization through interaction with the actin–binding protein cap 32/34," *The EMBO Journal*, 12(10):3763–3771 (1993).

Johnson, D.W., et al., "Development of a PCR Protocol for Sensitive Detection of Cryptosporidium Oocysts in Water Samples," *Applied and Environmental Microbiology*, 61(11): 3849–55 (1995).

Khramtsov, N.V., et al. "Cloning and Analysis of a *Cryptosporidium parvum* Gene Encoding a Protein with Homology to Cytoplasmic Form HSP 70," *Journal of Eukaryotic Microbiology* 42:416–422 (1995).

Kumar, Nirbhay et al., "*Plasmodium falciparum* gene encoding a protein similar to the 78–kDa rat glucose–regulated stress protein," *Biochemistry*, 85:6277–6281 (1988).

Kwoh, et al., "Transcription–based amplification system and detection of amplified human immunodeficiency virus type 1 with a bead–based sandwich hybridization format," *Proc. Natl. Acad. Sci. USA*, 86:1173–1177 (1989).

Laxer, M.A. et al., "DNA Sequences for the Specific Detection of *Cryptosporidium parvum* by the Polymerase Chain Reaction,", *American Journal of Tropical Medicine and Hygiene*, 45:688–694 (1991).

Le Chevallier, M.W. et al., "Giardia and Cryptosporidium spp. in Filtered Drinking Water Supplies," *Applied and Environmental Microbiology*, 57(9):2617–21 (1991).

Leng, X. et al., "Simplified Method for Recovery and PCR Detection of Cryptosporidium DNA from Bovine Feces," *Appl. Environ. Microbiol.*, 62(2):643–647 (1996).

Mahbubani, M.H., et al., "Detection of Giardia Cysts by Using the Polymerase Chain Reaction and Distinguishing Live from Dead Cysts," *Applied and Environmental Microbiology*, 57(12):3456–3461 (1991).

MacKenzie, W.R., et al., A Massive Outbreak in Milwaukee of cryptosporidium Infection Transmitted Through the Public Water Supply [published erratum appears in *New England Journal of Medicine* Oct. 13, 331(15):1035 (1994)]; *New England Journal of Medicine*, 331(3):161–7 (1994).

Maresca, B. et al., "The biology of the Heat Shock Response in Parasites," *Parasitology Today* 8(8):260–266 (1992).

Myers, T.W. et al., "Reverse Transcription and DNA Amplification by a *Thermus Thermophilus* DNA Polymerase," *Biochemistry*, 30:7661–7666, (1991).

Rashtchian, A. et al, "Immunological Capture of Nucleic Acid Hybrids and Application to Nonradioactive DNA Probe Assays," *Clinical Chemistry*, 33:1526:1530 (1987).

Rochelle et al., "Evaluation of Immunomagnetic Separation for Recovery of Infectious *Cryptosporidium parvum* Oocysts From Environmental Samples," *Applied and Environmental Microbiology*, 65(2):841–845, (Feb. 1999).

Rose, et al., Survey of Potable Water Supplies for Cryptosporidium and Giardia, *Environ. Sci. and Technol.*, 25:1393–1400 (1991).

Rose, et al., "Waterborne Cryptosporidiosis: Incidence, Outbreaks, and Treatment Strategies," *Cryptosporidium and Cryptosporidiosis*, Chapter 4, CRC Press, pp. 93–103 (1997).

Sheppard, Michael et al., "High level homology between a *Plasmodium chabaudi* heat shock protein gene and its *Plasmodium falciparum* equivalent," *Molecular and Biochemical Parasitology*, 33:101–104 (1989).

Taghi–Kilani et al., "Three tandemly repeated 5S ribosomal RNA–encloding genes identified, and characterized from *Cryptosporidium parvum,*" *Gene*, 142:253–258 (1994).

United States Environmental Protection Agency, "Method 1622: Cryptosporidium in Water by Filtration/FA," EPA 821–R–99–001, (Jan., 1999).

Upton, S.J. et al., "Comparative development of *Cryptosporidium parvum* (Apicomplexa) in 11 continuous host cell lines," *FEMS Microbiology Letters*, 118:223–236 (1994).

Wagner–Weining, C. et al., "Detection of Viable *Cryptosporidium parvum* Oocysts by PCR," *App. And Environ. Microbiol.*, 61(12):4514–4516 (1995).

Walker, G.T. et al., "Isothermal In Vivo Amplification to DNA by a Restrictive Enzyme/DNA Polymerase System," *Prop. Natl. Acad. Sci. USA*, 89:392–396 (1992).

Webster, K.A. et al., "Detection of *Cryptosporidium parvum* using a specific polymerase chain reaction," *Veterinary Parasitology*, 50:35–44 (1993).

Weiss, J.B., "PCR Dection of *Giardia lamblia,*" pp. 480–485 (1993). In: D.H. Pershing, T.F. Smith, F.C. Tenover & T.J. White (eds.), Diagnostic Molecular Microbiology: Principles and Applications.

\* cited by examiner 1 2 3 4 5 6 7

1 2 3 4 5 6 7 8

SEQUENCE LISTING

```
<160> NUMBER OF SEQ ID NOS: 11

<210> SEQ ID NO 1
<211> LENGTH: 3607
<212> TYPE: DNA
<213> ORGANISM: Cryptosporidium parvum

<400> SEQUENCE: 1
gaattctcat tctatggtga aaggtatata ttataaaatt tgtaatatta taataaaata      60 ttttttttcct atgaaattta attttacaag cattagtttc ataatataat catattgttg    120
attagtctgt aaaaatatta tttgattgat gaggagatcc atattcactt tattttatta    180
gaatttttat taaataaaag ttgtattatt tttttttttat tgtaattatt aaaaataatg    240
gccttttttt ttaattaata gaatattat gtagtgaatt acaatcacaa cttgatttta     300 ccatttatt atattttttt taaaaattat tgtaattatt taatactttta cacacgtaat    360 ttattttctt ctattgaatt aattaaactt tattcctata acattcatat acagttgcat    420
tgcaaatttt gcatgcaatg catgcatcaa tgtggacaaa ttttaataac gaagcatgaa    480
caacaacatg gcggttagct gctaaagtca aatatttaca ttaattatta ttataagaaa    540
acgaggagtt gatttattcg gaaagtaaag tgataaaagt aaatggaaaa aagggagaaa    600
atgaggaata agagggggaa gaaatgaaag aaagaaaaat ataagagaaa gaatgggaag    660
agtagtagta ggaagaagga aacaatgtag tgggaaatat aacgcaataa aaaaaaatgg    720
acgctacatg agggaagttt gaaatagttg ataattaaaa attttaattt aagtacaatt    780
tttaattcga tttcaatcta caaatactaa ttagagaaaa ttatatgcaa tattttttttt   840 ccatgttata gaaaattgaa gggtttaggc gccaaatcga gagttactac tttgtataaa    900
ataatttata tattaattgc gcattaaata aaaattaggg ggtttggcgg taattctgag    960
acgcaataat atttaaaata ataataaata atcaaaatat ataagaaaat gtaaatataa   1020
taaatgatga agaataatgg tcagttgtta agtacgtata aaatggcaaa tactaatcaa   1080
aatgtaaaaa ataaatagta taatgtcaaa ttatgaataa gaaataatag acacagctat   1140
ttatgagggg aaaagtcaat gtgtctcgta aagattgaaa aataagtaca agttatttta   1200
tctcactaga taaatagttt atttcatttt aactgattta ataaattctt atcgaaattc    1260
aaaaaaacaa gatgacatca tctgaaggtc cagctattgg tattgattta ggtaccacat   1320
```

-continued

```
actcatgtgt tggtgtatgg agaaacgata ctgtagatat tgttccaaac gatcaaggta      1380
accgtacaac accatcatat gtagcattta cagaaactga gcgtcttatt ggtgatgcag      1440
caaagaacca agttgctaga aacccagaaa atacagtttt tgatgctaaa cgtcttattg      1500
gtagaaagtt tgatgatcag gcagtacaaa gtgatatgac tcactggcca tttaaagtag      1560
ttagaggtcc aaaggacaag ccaatcatca gtgtaaacta cttaggtgaa agaaggaat       1620 tccatgctga agaaatttct gctatggctt acaaaagat gaaggagatc tctgaagcat       1680
acttgggtcg ccaaattaag aacgctgtag ttactgttcc agcttatttc aatgactcac      1740
agcgtcaagc aacaaaggat gcaggtgcaa ttgctggttt gaatgtaatg agaatcatta      1800
acgagccaac tgcagctgct attgcttatg gtcttgataa gaaaggaact ggcgagagaa      1860
atgtattgac tttcgattta ggtggtggta cttttgatgt atcattatta actattgaag      1920
atggtatttt tgaagttaaa gctaccgctg gtgatactca cttgggtggt gaagattttg      1980
ataacagact cgtagaattc tgtgtacaag atttcaagag aaagaataga ggtatggatt      2040
taacctcaaa tgctagagct ttaagaagac tcagaactca atgcgagcgt gcaaagagaa      2100
ctttgtcatc ttctactcaa gctacaattg agttagattc actctatgaa ggtattgatt      2160
attcagttgc catcagtaga gctagattcg aagaactctg cgccgattac ttccgtgcaa      2220
ctttagctcc agttgagaaa gtactcaagg atgctggtat ggacaagaga tctgtacatg      2280
atgttgtatt ggttggtggt tctacacgta ttccaaaggt tcaggccttg attcaggaat      2340 tcttttaacgg taaagagcca tgcaaagcaa tcaatccaga cgaagctgtt gcttatggtg      2400
ctgctgtaca agctgctatc ttaaatggtg agcaatcctc tgccgtacag gatctcttat      2460
tattggatgt tgctccatta tcactcggtt tagaaactgc tggtggtgtt atgaccaagc      2520
ttattgaacg taatacaact atcccagcaa agaagcacac agtcttcact acttatgctg      2580
ataaccagag tggtgtcttg atccaagttt atgagggtga gagagccatg actaaggata      2640
accatctcct cggaaagttc catcttgatg gtattccacc agcaccaaga ggtgtaccac      2700
aaattgaagt cacctttgat attgatgcta atggtatctt gaatgtgtct gctgttgata      2760
agagtactgg taagagcagc aagatcacta ttactaacga taagggtaga ttatcaaagg      2820
tatctgatat tgaacgtatg gttaatgatg ctgagaaata caagggtgag gatgagcaga      2880
acagacttaa gattgaggct aagaactctt tggagaacta cctctataac atgaggaaca      2940
ccatccaaga accaaaggtt aaggaaaagc tttctcaatc tgaaattgat gaggctgaga      3000
agaagatcaa ggatgctctt gactggctcg agcacaacca aactgctgaa aaggacgagt      3060
ttgaacatca acaaaaggag attgaaactc atatgaatcc actcatgatg aagatctact      3120
ctgctgaggg tggtatgcca ggtggaatgc caggtggtat gccaggcggt atgccaggtg      3180
gaatgccagg tggtatgcca ggtggaatgc caggcggtat gccaggtggt atgccaggtg      3240
gtatgccagg tggtatgcca ggatctaatg gtccaactgt tgaagaggtc gactaattat      3300
tttagtcacc aaaaaaactc actcaaaatg gaaagttaag aactatttac acactttcaa      3360
tttctagtta ttttttacca aaataagaag aaaagcacac tctaccttta ggctatattt      3420
tccattctct agcctagact cccttatatg cgagttggca atatttcacc agatttaccg      3480
ccataaattt ggcatttttg gcttattgat agtcattact attatcaata cgagttctcg      3540
aaaagagaaa ggccagatat ctggatagtt tggaacaaac tatgttctct agtttatttg      3600
agaattc                                                                3607
```

<210> SEQ ID NO 2
<211> LENGTH: 21
<212> TYPE: DNA
<213> ORGANISM: Cryptosporidium parvum

<400> SEQUENCE: 2
ctgttcctta tggtgctgct g                                            21

<210> SEQ ID NO 3
<211> LENGTH: 21
<212> TYPE: DNA
<213> ORGANISM: Cryptosporidium parvum

<400> SEQUENCE: 3
cctcttggtg ctggtggaat a                                            21

<210> SEQ ID NO 4
<211> LENGTH: 20
<212> TYPE: DNA
<213> ORGANISM: Cryptosporidium parvum

<400> SEQUENCE: 4
aaatggtgag caatcctctg                                              20

<210> SEQ ID NO 5
<211> LENGTH: 20
<212> TYPE: DNA
<213> ORGANISM: Cryptosporidium parvum

<400> SEQUENCE: 5
cttgctgctc ttaccagtac                                              20

<210> SEQ ID NO 6
<211> LENGTH: 48
<212> TYPE: DNA
<213> ORGANISM: Cryptosporidium parvum

<400> SEQUENCE: 6
aattctaata cgactcacta tagggagact tgctgctctt accagtac               48

<210> SEQ ID NO 7
<211> LENGTH: 21
<212> TYPE: DNA
<213> ORGANISM: Giardia sp.

<400> SEQUENCE: 7
agggctccgg cataactttc c                                            21

<210> SEQ ID NO 8
<211> LENGTH: 20
<212> TYPE: DNA
<213> ORGANISM: Giardia sp.

<400> SEQUENCE: 8
gtatctgtga cccgtccgag                                              20

<210> SEQ ID NO 9
<211> LENGTH: 23
<212> TYPE: DNA
<213> ORGANISM: Cryptosporidium parvum

<400> SEQUENCE: 9
aaatggtgag caatcctctg ccg                                          23

```
-continued

<210> SEQ ID NO 10
<211> LENGTH: 20
<212> TYPE: DNA
<213> ORGANISM: Cryptosporidium parvum

<400> SEQUENCE: 10
ccattatcac tcggtttaga                                              20

<210> SEQ ID NO 11
<211> LENGTH: 21
<212> TYPE: DNA
<213> ORGANISM: Giardia sp.

<400> SEQUENCE: 11
caggccttgg cgttcccgaa g                                            21
```

CRYPTOSPORIDIUM DETECTION METHOD

CROSS-REFERENCE TO RELATED APPLICATIONS

This Application is a continuation-in-part of U.S. patent application Ser. No. 09/100,649, filed Jun. 8, 1998 and entitled CRYPTOSPORIDIUM DETECTION METHOD, now abandoned; which is a continuation of U.S. patent application Ser. No. 08/647,351, filed May 9, 1996 and entitled CRYPTOSPORIDIUM DETECTION METHOD, now U.S. Pat. No. 5,770,368 which issued on Jun. 23, 1998; and is also a continuation-in-part of PCT Application PCT/US97/07972, filed May 8, 1997 and entitled CRYPTOSPORIDIUM DETECTION METHOD, the contents of which are incorporated herein in their entirety.

BACKGROUND

Protozoan parasites are a major cause of gastrointestinal disease. Within the last decade, the protozoa Cryptosporidium and Giardia have been increasingly associated with waterborne outbreaks of acute diarrhea. *Cryptosporidium parvum* is of particular concern because no known treatment of the illness is available at present. Moreover, in the immunocompromised host, a *C. parvum* infection can lead to prolonged severe diarrhea, malnutrition, wasting, and death.

Cryptosporidium is an enteric coccidia, which has a multi-staged life cycle one to eight days in duration. The oocyst contains four sporozoites which, during normal infection, are released in the presence of bile salts and proteases. The sporozoites attach and penetrate intestinal epithelial cells. Once inside, they develop into a rounded trophozoite in the area between the cytoplasmic membrane and the cytoplasm. Through asexual reproduction, the trophozoite (a type I meront) forms up to eight merozoites. The merozoites may then develop into a type II meront, which, by asexual reproduction, forms four merozoites. The second generation merozoites may develop into male (microgamont) or female (macrogamont) forms. The male form may lead to the sexual phase of the Cryptosporidium life cycle which culminates, in vivo, in the production of the environmentally resistant oocysts. These hardy structures possess a thick, double-layered protective cell wall which is resistant to most disinfectants, chlorine concentrations generally present in municipal water supplies, and temperatures between −4° C. and 42° C.

Cryptosporidium is prevalent in most vertebrate groups. Domestic animals, such as rodents, kittens, puppies, and calves may constitute an important reservoir of the human Cryptosporidium. However, disease outbreaks in day-care centers, hospitals and urban family groups indicate that most human infections are transmitted person-to-person rather than via a zoonotic route. Since oocysts are found almost exclusively in stool, the transmission is undoubtedly fecal-oral. Moreover, the recovery of oocysts from both surface and drinking water suggests that indirect transmission via water is not uncommon.

Quantitative studies on the infectious dose for humans are currently limited. One study found that, in healthy volunteers, the infectious dose ($ID_{50}$) is 132 oocysts, with as few as 30 oocysts causing infection in 20% of individuals tested (DuPont et al., 1995). However, the $ID_{50}$ could be lower, such as one to ten oocysts, in more susceptible individuals.

Indeed, Cryptosporidium has been documented as a major cause of waterborne illness on numerous occasions. The largest outbreak occurred during the spring of 1993 in Milwaukee, Wis., resulting in approximately 400,000 illnesses and 100 deaths (MacKenzie et al., 1994).

Over the last 10 years, Cryptosporidium oocysts have been found in 9.1 to 100% of surface waters tested at concentrations ranging from 0.003 to 1,920 oocysts per liter. Oocysts were also detected in 27% and 17% of finished water samples in two multi-state surveys.

These studies, surveys, and documented outbreaks clearly indicate that infectious Cryptosporidium may be found in source water and the efficiency of conventional water treatment needs to be closely monitored. Indeed, the occurrence of the causative agents *Cryptosporidium parvum* and *Giardia lamblia* in water supplies has become a critical issue for the water industry.

The current techniques for isolating Cryptosporidium and Giardia from water involve filtration and centrifugation to concentrate and purify oocysts and cysts, respectively, followed by immunofluorescence microscopy. Objects with the correct shape, dimensions, and fluorescence are confirmed by observation of internal structures using differential interference contrast microscopy. The limitations of these procedures include loss of oocysts or cysts during isolation, resulting in recovery efficiencies ranging from 100 percent to less than one percent for Cryptosporidium. Moreover, the immunofluorescent assay (IFA) method cannot distinguish viable and potentially infective from non-viable or non-infective oocysts and cysts. Additional limitations of IFA include nonspecific antibody binding and cross-reactive antibody binding among human and animal infective species of Cryptosporidium or Giardia.

For the foregoing reasons, there is a need for an alternative method of detecting Cryptosporidium and Giardia pathogens that is rapid, sensitive, and specific. Moreover, the alternative method would be able to determine if Cryptosporidium oocysts are viable and infective.

SUMMARY

The present invention includes a method for selectively detecting the presence of *C. parvum* organisms in a sample potentially containing *C. parvum* organisms and other Cryptosporidium organisms. The method comprises, first, selectively amplifying at least a portion of *C. parvum* HSP70 polynucleotide present in the sample using a primer, and then, detecting the presence of any amplified polynucleotide formed. The presence of amplified polynucleotide indicates the presence of *C. parvum* organisms in the sample. The method can additionally comprise recovering *C. parvum* oocysts from the sample, prior to amplifying the *C. parvum* polynucleotide. Further, the method can additionally comprise extracting *C. parvum* DNA from the recovered oocysts, prior to amplifying the *C. parvum* polynucleotide.

In a preferred embodiment, the primer has a sequence selected from the group consisting of SEQ ID NO:4, SEQ ID NO:5 and SEQ ID NO:6. In another preferred embodiment, the amplification is performed by a temperature cycling amplification reaction, such as a polymerase chain reaction. Alternately, the amplification is performed by an isothermal amplification reaction, such as a self-sustained sequence replication reaction.

In a preferred embodiment, the detecting is performed by subjecting the amplified polynucleotide to hybridization conditions with a DNA probe or with a PNA probe, such as a probe having a sequence selected from the group consisting of SEQ ID NO:9, SEQ ID NO: 10, the complement of SEQ ID NO:9 and the complement of SEQ ID NO:10.

The present invention also includes a method for selectively detecting the presence of C. parvum organisms and for detecting the presence of G. lamblia organisms, simultaneously, in a sample potentially containing C. parvum organisms and G. lamblia organisms, and where the sample also potentially contains other Cryptosporidium species organisms. The method comprises, first, amplifying at least a portion of the G. lamblia HSP polynucleotide present in the sample using a first primer, and selectively amplifying at least a portion of the C. parvum HSP70 polynucleotide-present in the sample using a second primer, and then detecting the presence of any amplified polynucleotide formed. The presence of amplified C. parvum HSP70 polynucleotide indicates the presence of C. parvum organisms in the sample, and the presence of amplified G. lamblia HSP polynucleotide indicates the presence of G. lamblia organisms in the sample. The method can additionally comprise recovering C. parvum oocysts or G. lamblia cysts from the sample, prior to amplifying the C. parvum polynucleotide. Further, the method can additionally comprise extracting C. parvum DNA from the recovered oocysts or G. lamblia DNA from the recovered cysts prior to amplifying the C. parvum polynucleotide or the G. lamblia polynucleotide.

In a preferred embodiment, the first primer has a sequence selected from the group consisting of SEQ ID NO:7 and SEQ ID NO:8, and the second primer has a sequence selected from the group consisting of SEQ ID NO:4, SEQ ID NO:5 and SEQ ID NO:6. In another preferred embodiment, the amplification is performed by a temperature cycling amplification reaction, such as a polymerase chain reaction. Alternately, the amplification is performed by an isothermal amplification reaction, such as a self-sustained sequence replication reaction.

In a preferred embodiment, the detecting is performed by subjecting the amplified polynucleotide to hybridization conditions with a DNA probe or with a PNA probe, such as a probe having a sequence selected from the group consisting of SEQ ID NO:9, SEQ ID NO:10, SEQ ID NO:11, the complement of SEQ ID NO:9, the complement of SEQ ID NO:10 and the complement of SEQ ID NO:11.

The present invention further includes a method for selectively detecting viable C. parvum organisms in a sample potentially containing viable C. parvum organisms and other Cryptosporidium organisms. The method comprises, first, inducing mRNA transcription of C. parvum heat shock protein 70 (HSP70) DNA, and then, producing a C. parvum HSP70 polynucleotide, such as at least one copy of the mRNA or cDNA, from at least a portion of the C. parvum HSP70 mRNA utilizing a primer. Next, at least a portion of the C. parvum HSP70 polynucleotide is selectively amplified and the presence of any amplified polynucleotide formed is detected. The presence of amplified polynucleotide indicates the presence of viable C. parvum organisms in the sample. The method can additionally comprise recovering C. parvum oocysts from the sample, prior to amplifying the C. parvum polynucleotide. Further, the method can additionally comprise extracting C. parvum DNA from the recovered oocysts, prior to amplifying the C. parvum polynucleotide.

In a preferred embodiment, the primer has a sequence selected from the group consisting of SEQ ID NO:4, SEQ ID NO:5 and SEQ ID NO:6. In another preferred embodiment, the amplification is performed by a temperature cycling amplification reaction, such as a polymerase chain reaction. Alternately, the amplification is performed by an isothermal amplification reaction, such as a self-sustained sequence replication reaction.

In a preferred embodiment, the detecting is performed by subjecting the amplified polynucleotide to hybridization conditions with a DNA probe or with a PNA probe, such as a probe having a sequence selected from the group consisting of SEQ ID NO:9, SEQ ID NO:10, the complement of SEQ ID NO:9 and the complement of SEQ ID NO:10.

The present invention also includes a method for selectively detecting viable C. parvum organisms and for detecting viable G. lamblia organisms, simultaneously, in a sample potentially containing C. parvum organisms and G. lamblia organisms, and where the sample also potentially contains other Cryptosporidium species organisms. The method comprises, first, inducing mRNA transcription of C. parvum heat shock protein 70 (HSP70) DNA, and inducing mRNA transcription of a G. lamblia heat shock protein DNA, and then, producing a G. lamblia HSP polynucleotide, such as at least one copy of the mRNA or cDNA, from at least a portion of the G. lamblia HSP mRNA utilizing a first primer, and selectively producing a C. parvum HSP70 polynucleotide, such as at least one copy of the mRNA or cDNA, from at least a portion of the C. parvum HSP70 mRNA utilizing a second primer. Next, at least a portion of the G. lamblia HSP polynucleotide produced is amplified and at least a portion of the C. parvum HSP70 polynucleotide produced is amplified and the presence of any amplified polynucleotide formed is 25 detected. The presence of amplified C. parvum HSP70 polynucleotide indicates the presence of viable C. parvum organisms in the sample, and the presence of amplified G. lamblia HSP polynucleotide indicates the presence of viable G. lamblia organisms in the sample. The method can additionally comprise recovering C. parvum oocysts or G. lamblia cysts from the sample, prior to amplifying the C. parvum polynucleotide. Further, the method can additionally comprise extracting C. parvum DNA from the recovered oocysts or G. lamblia DNA from the recovered cysts prior to amplifying the C. parvum polynucleotide or the G. lamblia polynucleotide.

In a preferred embodiment, the first primer has a sequence selected from the group consisting of SEQ ID NO:7 and SEQ ID NO:8, and the second primer has a sequence selected from the group consisting of SEQ ID NO:4, SEQ ID NO:5 and SEQ ID NO:6. In another preferred embodiment, the amplification is performed by a temperature cycling amplification reaction, such as a polymerase chain reaction. Alternately, the amplification is performed by an isothermal amplification reaction, such as a self-sustained sequence replication reaction.

In another preferred embodiment, the detecting is performed by subjecting the amplified polynucleotide to hybridization conditions with a DNA probe or with a PNA probe, such as a probe having a sequence selected from the group consisting of SEQ ID NO:9, SEQ ID NO:10, SEQ ID NO:11, the complement of SEQ ID NO:9, the complement of SEQ ID NO:10 and the complement of SEQ ID NO:11.

The present invention additionally includes a method for selectively detecting infectious C. parvum organisms in a sample potentially containing infectious C. parvum organisms and other Cryptosporidium organisms. The method comprises, first, inoculating a cell culture with the sample, where the cell culture is susceptible to infection by infectious C. parvum organisms, and exposing the inoculated cell culture to conditions suitable to induce mRNA transcription of C. parvum heat shock protein 70 (HSP70) DNA. Next, a C. parvum HSP70 polynucleotide, such as at least one copy of the mRNA or cDNA, is produced from at least a portion of the C. parvum HSP70 mRNA utilizing a first primer and the C. parvum HSP70 polynucleotide produced is selectively amplified. Then, the presence of any amplified polynucleotide formed is detected. The presence of amplified polynucleotide indicates the presence of infectious *C. parvum* organisms in the sample. In one embodiment, the cell culture comprises a number of cells, the sample comprises a number of infective oocysts, and the number of cells exceeds the number of infective oocysts.

In a preferred embodiment, the first primer has a sequence selected from the group consisting of SEQ ID NO:4, SEQ ID NO:5 and SEQ ID NO:6. In another preferred embodiment, the amplification is performed by a temperature cycling amplification reaction, such as a polymerase chain reaction. Alternately, the amplification is performed by an isothermal amplification reaction, such as a self-sustained sequence replication reaction. Further, the amplification can be performed in-situ.

In another preferred embodiment, the detecting is performed by subjecting the amplified polynucleotide to hybridization conditions with a DNA probe or with a PNA probe, such as a probe having a sequence selected from the group consisting of SEQ ID NO:9, SEQ ID NO:10, the complement of SEQ ID NO:9 and the complement of SEQ ID NO:10. Further, the detecting can be performed in-situ.

In a particularly preferred embodiment, the method additionally comprises detecting viable *G. lamblia* organisms in the sample, simultaneously with selectively detecting infectious *C. parvum*. In this embodiment, the method additionally comprises inducing mRNA transcription of mRNA transcription of a *G. lamblia* heat shock protein DNA. Then, a *G. lamblia* HSP polynucleotide, such as at least one copy of the mRNA or cDNA, is produced from at least a portion of the *G. lamblia* HSP mRNA utilizing a second primer and at least a portion of the *G. lamblia* HSP polynucleotide produced is amplified. The presence of any amplified polynucleotide formed is detected and the presence of amplified *G. lamblia* HSP polynucleotide indicates the presence of viable *G. lamblia* organisms in the sample. The method can additionally comprise recovering *G. lamblia* cysts from the sample, prior to amplifying the *G. lamblia* HSP polynucleotide.

In a preferred embodiment, the second primer has a sequence selected from the group consisting of SEQ ID NO:7 and SEQ ID NO:8. In another preferred embodiment, the amplification is performed by a temperature cycling amplification reaction, such as a polymerase B chain reaction. Alternately, the amplification is performed by an isothermal amplification reaction, such as a self-sustained sequence replication reaction.

In another preferred embodiment, the detecting is performed by subjecting the amplified polynucleotide to hybridization conditions with a DNA probe or with a PNA probe, such as a probe having a sequence selected from the group consisting of consisting of SEQ ID NO:11 and the complement of SEQ ID NO:11.

The present invention also includes a method for selectively detecting infectious *C. parvum* organisms in a sample potentially containing infectious *C. parvum* organisms and other Cryptosporidium organisms. The method comprises, first, inoculating a cell culture with the sample, where the cell culture is susceptible to infection by infectious *C. parvum* organisms. Then, the inoculated cell culture is exposed to conditions suitable to induce mRNA transcription of *C. parvum* heat shock protein 70 (HSP70) DNA. Next, the presence of transcribed mRNA is selectively detected. The presence of amplified polynucleotide detected indicates the presence of infectious *C. parvum* organisms in the sample. The detection can be performed by subjecting the amplified polynucleotide to hybridization conditions with a DNA probe, such as a DNA or PNA probe has a sequence selected from the group consisting of SEQ ID NO:9, SEQ ID NO:10, the complement of SEQ ID NO:9 and the complement of SEQ ID NO:10. Further, the detecting can be performed in-situ. Finally, the cell culture can comprise a number of cells, the sample comprises a number of infective oocysts, and the number of cells can exceed the number of infective oocysts.

The present invention also includes a kit for selectively detecting *C. parvum*. The kit comprises a first primer and a second primer for amplification of a portion of *C. parvum* HSP70 mRNA that is specific for *C. parvum*, and a PNA probe for detection of the amplified portion of *C. parvum* HSP70 polynucleotide. The first primer or the second primer can have a sequence selected from the group consisting of SEQ ID NO:4, SEQ ID NO:5 and SEQ ID NO:6. The probe can have a sequence selected from the group consisting of SEQ ID NO:9, SEQ ID NO:10, the complement of SEQ ID NO:9 and the complement of SEQ ID NO:10.

The present invention further includes a kit for detecting *C. parvum* and *G. lamblia*. The kit comprises a first primer and a second primer for amplification of a portion of *C. parvum* HSP70 mRNA that is specific *C. parvum*, a third primer and a fourth primer for amplification of a target sequence of *G. lamblia*, and a PNA probe for detection of the amplified portion of *C. parvum* HSP70 polynucleotide. The kit can further comprise a PNA probe for detection of the amplified portion of the target sequence from *G. lamblia*. The first primer or the second primer can have a sequence selected from the group consisting of SEQ ID NO:4, SEQ ID NO:5 and SEQ ID NO:6. The third primer or the fourth primer can have a sequence selected from the group consisting of SEQ ID NO:7 and SEQ ID NO:8. Further, the probe can have a sequence selected from the group consisting of SEQ ID NO:9, SEQ ID NO:10, SEQ ID NO:11, the complement of SEQ ID NO:9, the complement of SEQ ID NO:10 and the complement of SEQ ID NO:11.

BRIEF DESCRIPTION OF THE DRAWINGS

These and other features, aspects, and advantages of the present invention will become better understood with regard to the following description, appended claims and accompanying drawings where:

DESCRIPTION

Figure 1:
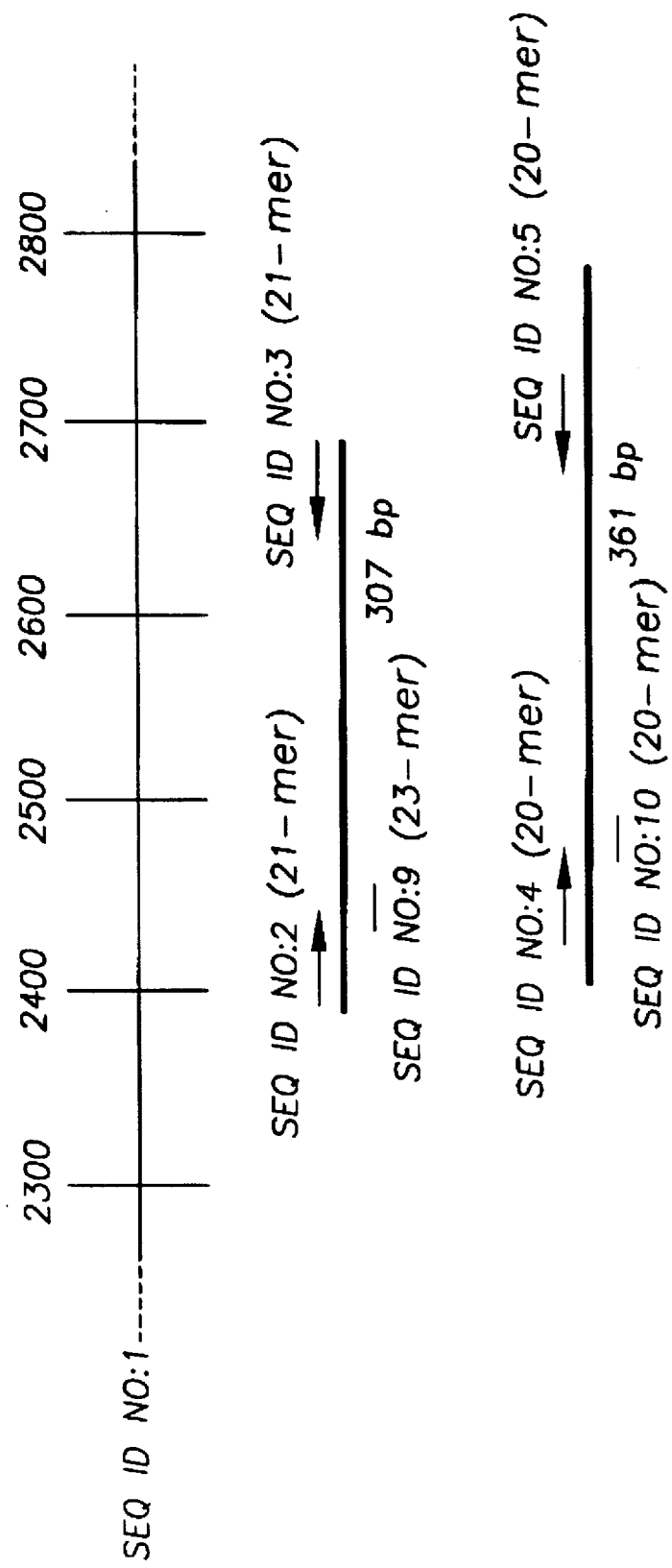
FIG. 1 is a diagram showing the relative map positions of primer pair SEQ ID NO:2 and SEQ ID NO:3, primer pair SEQ ID NO:4 and SEQ ID NO:5, probe SEQ ID NO:9, and probe SEQ ID NO: 10 within the HSP70 gene sequence SEQ ID NO:1.

Parasites of mammals experience an increase in environmental temperature when the parasitic microorganisms infect a host organism because the body temperature of the host organism is higher than that of the surrounding environment. The physiological response of parasitic microorganisms to this increased temperature is called the "heat shock response" and is characterized by transcription of heat shock protein (HSP) genes above a base line. The heat shock response has a fundamental role during host invasion by both *Cryptosporidium parvum* and *Giardia lamblia*.

Since HSP gene transcription is a physiological response of living cells to an environmental stimulus, the presence of viable organisms is detected by identifying the presence of the HSP gene transcripts in a sample. Additionally, infective organisms are detected by inoculating susceptible cell cultures with the appropriate form of the parasitic microorganism and detecting the presence of the HSP gene transcripts produced during the infection of the cell cultures.

The present invention involves methods for the detection of *Cryptosporidium parvum* in water. In one embodiment, there is provided a method for detecting the mere presence of *Cryptosporidium parvum* in water. In another embodiment, there is provided a method for detecting the presence of viable *Cryptosporidium parvum* in water. In yet another embodiment, there is provided a method for detecting the presence of infective *Cryptosporidium parvum* in water.

The present invention also includes methods for the detection of *Giardia lamblia* in water. In one embodiment, there is provided a method for detecting the mere presence of *Giardia lamblia* in water, in addition to detecting the presence of *Cryptosporidium parvum*. In another embodiment, there is provided a method for detecting the presence of viable *Giardia lamblia* in water, in addition to detecting the presence of viable *Cryptosporidium parvum*. In yet another embodiment, there is provided a method for detecting the presence of viable *Giardia lamblia* in water, in addition to detecting the presence of infective *Cryptosporidium parvum.*

In summary, the methods of the present invention are performed as follows. The mere presence of *Cryptosporidium parvum* is determined by, first, recovering *Cryptosporidium parvum* oocysts from a potentially contaminated water sample by appropriate concentration methods or by Method 1622. Next, the *Cryptosporidium parvum* DNA from the sample is extracted and amplified, and the amplicons are detected using appropriate methods such as hybridization with DNA or PNA probes. In a preferred embodiment, the mere presence of *Giardia lamblia* is simultaneously determined with determining the mere presence of *Cryptosporidium parvum* by extracting the *Giardia lamblia* DNA from the sample, amplifying the DNA and detecting the amplified DNA using appropriate methods such as probing with DNA or PNA probes, in conjunction with the corresponding procedures for determining the presence of *Cryptosporidium parvum.*

The presence of viable *Cryptosporidium parvum* is determined by, first, recovering *Cryptosporidium parvum* oocysts from a potentially contaminated water sample by appropriate methods such as by concentration or by Method 1622. Next, expression of *Cryptosporidium parvum* HSP70 mRNA is induced from viable *Cryptosporidium parvum* organisms such as by incubation of the recovered oocysts at between about 37 to 42° C. Then, the expressed mRNA is extracted and amplified; or the expressed mRNA is extracted, reverse transcribed into cDNA and the cDNA is amplified. Finally, the amplicons are detected using appropriate methods such as hybridization with DNA or PNA probes. In a preferred embodiment, the presence of viable *Giardia lamblia* is simultaneously determined with determining the presence of viable *Cryptosporidium parvum* by inducing the expression of a *Giardia lamblia* HSP mRNA, and extracting and amplifying the expressed mRNA; or by extracting the expressed mRNA, reverse transcribing the mRNA into cDNA and amplifying the cDNA; and then detecting the amplicons using appropriate methods such as hybridization with DNA or PNA probes, in conjunction with the corresponding procedures for determining the presence of viable *Cryptosporidium parvum.*

The presence of infective *Cryptosporidium parvum* is determined by, first, recovering *Cryptosporidium parvum* oocysts from a potentially contaminated water sample by appropriate concentration methods or by Method 1622. Next, appropriate host cell monolayers are inoculated with the recovered oocysts, and the inoculated monolayers are incubated for between about 24 and 72 hours to permit infection of cells and expression of HSP70 mRNA. Then, the expressed HSP70 mRNA is extracted and amplified; or the expressed mRNA is extracted and reverse transcribed into cDNA and the cDNA is amplified. Finally, the amplicons are detected using appropriate methods such as hybridization with DNA or PNA probes. In another embodiment, instead of extracting the expressed HSP70 mRNA, the presence of the expressed HSP70 mRNA is detected in-situ by hybridization with DNA or PNA probes; or the expressed HSP70 mRNA is amplified in-situ and the amplicons are detected in-situ by hybridization with DNA or PNA probes. In yet another embodiment, infectivity is quantified. In a preferred embodiment, the presence of viable *Giardia lamblia* is simultaneously determined with determining the presence of infective *Cryptosporidium parvum* by inducing the expression of a *Giardia lamblia* HSP mRNA, extracting the expressed mRNA and amplifying it directly or reverse transcribing the mRNA into cDNA and amplifying the cDNA, and detecting the amplicons using appropriate methods such as hybridization with DNA or PNA probes, in procedures corresponding to those for determining the presence of viable *Cryptosporidium parvum.*

As used herein, "polynucleotide" refers to either DNA, including cDNA, or mRNA.

The procedures used in the methods of the present invention will now be described in greater detail.

I. RECOVERY OF CRYPTOSPORIDIUM PARVUM OOCYSTS AND GIARDIA LAMBLIA CYSTS

In a preferred embodiment of the present invention, the procedure for recovering *C. parvum* oocysts and the *G. lamblia* cysts in a sample, such as potentially contaminated water or stool samples, is performed by any of a variety of concentration techniques. For example, a predetermined volume of potentially contaminated water, such as 100 liters, is filtered through a 1 μm nominal porosity yarn-wound polypropylene filter or its equivalent. The filtration flow rate is restricted to about 4 liters/minute. Sampled filters are typically shipped on ice to analytical laboratories for analysis within 24 hours.

Retained protozoa are eluted from the filter within 96 hours of collection. First, the filter fibers are cut, teased and washed in a buffered detergent solution by hand or with the aid of a stomacher. Oocysts or cysts recovered in the eluent are then concentrated by centrifugation and partially purified by flotation on a Percoll-sucrose solution with a specific gravity of 1.1.

In another preferred embodiment, *C. parvum* oocysts and *G. lamblia* cysts are recovered using Method 1622 for *C. parvum* oocysts, or by a corresponding method for *G. lamblia* cysts, as disclosed in EPA 821-R-99-001, January 1999, published by the United States Environmental Protection Agency, Office of Water, Washington, DC 20460, the contents of which are incorporated herein by reference in its entirety.

II. DETERMINATION OF THE MERE PRESENCE OF *C. PARVUM* AND *G. LAMBLIA* ORGANISMS

The mere presence of *C. parvum* is determined by, first, recovering *C. parvum* oocysts from a sample. Next, the *C. parvum* DNA from the sample is extracted and amplified, and the amplicons are detected using appropriate methods such as hybridization with DNA or PNA probes. In a preferred embodiment, the mere presence of *G. lamblia* is simultaneously determined with determining the mere presence of *C. parvum* using corresponding procedures to extract the *G. lamblia* DNA from the sample, to amplify the DNA and to detect the amplified DNA.

A. Recovery of Oocysts and Cysts

The mere presence of *C. parvum*, or *C. parvum* and *G. lamblia*, is determined by, first, recovering *C. parvum* oocysts and *G. lamblia* cysts from a potentially contaminated water sample or from another appropriate sample such as a host stool sample, as disclosed above.

B. Extraction of DNA

Next, the *C. parvum* DNA and *G. lamblia* DNA is extracted from the sample. The DNA is extracted from cysts and oocysts by any method capable of lysing the cysts and oocysts. In a preferred embodiment, the DNA is extracted by freezing the oocysts and cysts in liquid nitrogen for 2 minutes, followed by thawing at 95° C. for 5 minutes. The freeze/thaw cycle is repeated, if necessary, and the lysate is used directly for amplification reaction. In a preferred embodiment, RNA is removed from the lysate by treatment with DNase-free RNase A.

In another preferred embodiment, additional extraction steps are used to further purify the extracted DNA. For example, the cysts and oocysts cells are additionally lysed in 50 mM Tris-HCl, 20 mM EDTA, pH 8, containing 2 mg/ml proteinase K and 0.5% sarkosyl, and incubated at 37° C. for 1 h. Then, 5 M NaCl is added to a final concentration of 1 M, and CTAB (hexadecyltrimethyl ammonium bromide) is added to a concentration of 1% Following incubation at 65° C. for 30 minutes, the lysate is subjected to at least one freeze/thaw cycle, and phenol/chloroform extraction. The DNA is precipitated by the addition of 0.6 vol, of isopropanol and the DNA precipitate is then washed with 70% ethanol.

C. Amplification of the Extracted DNA

After extraction of the nucleic acid from the *C. parvum* oocysts and *G. lamblia* cysts, the nucleic acid is amplified using any suitable amplification technique, as will be understood by those with skill in the art with reference to the disclosure herein. These techniques include:

1) cycling probe technology (CPT) (Duck, G. et al., Probe Amplified System Based on Chimeric Cycling Oligonucleotides, BIOTECHNIQUES, 9:142–147, 1990);
2) ligase amplification reaction (LAR) (PCT Patent Publication No. 89/09835);
3) ligase chain reaction (LCR) (Barany, F., Genetic Disease Detection and DNA Amplification Using Cloned Thermostable Ligase; PROC. NATL. ACAD. SCI. USA, 88:189–193, 1991);
4) ligation activated transcription (LAT) (Rashtchian, A. et al., Immunological Capture of Nucleic Acid Hybrids and Application to Nonradioactive DNA Probe Assays, CLINICAL CHEMISTRY, 33:1526–1530, 1987);
5) nucleic acid sequence-based amplification (NASBA) (European Patent No EP 0329822);
6) polymerase chain reaction (PCR) (U.S. Pat. Nos. 4,683,195, 4,683,202, and 4,965,188);
7) Qβ replicase based amplification (U.S. Pat. No. 4,957,858);
8) reverse transcriptase PCR (RT-PCR) (Myers, T. W. et al., Reverse Transcription and DNA Amplification by a Thermus Thermophilus DNA Polymerase, BIOCHEMISTRY, 30:7661–7666, 1991);
9) self-sustained sequence replication (3SR) (U.S. Pat. No. 5,409,818, PCT Patent Publication No. 90/06995 and Guatelli, J. C. et al, Isothermal, In Vitro Amplification of Nucleic Acids by a Multienzyme Reaction Modeled After Retroviral Replication, PROC. NATL. ACAD. SCI. USA, 87:1874–1878, 1990);
10) strand displacement amplification (SDA) (Walker, G. T. et al., Isothermal In Vivo Amplification of DNA by a Restriction Enzyme/DNA Polymerase System; PROP. NATL. ACAD. SCI. USA 89:392–396; 1992); and
11) transcription-based amplification system (TAS) (Kwoh, D. Y. et al., Transcription-Based Amplification System and Detection of Amplified HIV Type 1 With a Bead-Based Sandwich Hybridization Fonnat; PROC. NATL. ACAD. ACI. USA, 86:1173–1177, 1989; U.S. Pat. No. 5,437,990).

i. Heat Cycling Amplification Reaction

In a preferred embodiment, the amplification technique used is heat cycling amplification reaction such as PCR. In the PCR amplification procedure, a target HSP nucleic acid sequence is amplified by treating the double-stranded polynucleotide with two oligonucleotide primers, each being complementary to one of the two strands. The primers hybridize with their complementary strands and extension products are synthesized using DNA polymerase and four different deoxynucleotide triphosphates. The DNA polymerase is preferably a thermostable enzyme, such as Taq, Tth, Pfu or any other native, mutated or deleted enzyme derived from a thermophilic organism. The extension products are separated from their complementary strands by denaturation at an elevated temperature, generally from about 80° to 100° C. The reaction mixture is repeatedly cycled between a low temperature annealing step, generally of from about 37° to 70° C., an intermediate temperature primer extension step, generally of from about 70° to 80° C., and a higher temperature denaturation step, generally of from about 80° to 100° C. If a thermostable DNA polymerase is used, the polymerase reaction is typically cycled 20–40 times without needing additional enzyme.

ii. Isothermal Amplification Reactions

In another preferred embodiment, the amplification technique used is an isothermal amplification reaction such as nucleic acid sequence-based amplification (NASBA) or strand displacement amplification (SDA). In a particularly preferred embodiment, the isothermal amplification reaction is performed using a self-sustaining sequence replication (3SR) amplification reaction.

Self-sustaining sequence replication amplification can produce a $10^7$-fold amplification of target nucleic acid in a typical 60 to 90 minute cycle and consists of isothermal cycles of replication of DNA and RNA at approximately 41° C. using the three enzymes, reverse transcriptase, RNase H, and an RNA polymerase such as T7 RNA polymerase. The reverse transcriptase converts a target RNA into an RNA-cDNA double strand, the RNase H digests the RNA component of the RNA-cDNA double strand, and the T7 polymerase produces numerous RNA transcripts from each cDNA template. The freshly generated RNA then serves as a template for the production of additional cDNA. 3SR amplification is preferably optimized to obtain maximum sensitivity and specificity. In one embodiment, the reaction is conducted in 15% DMSO at 41° C. for 60–90 minutes with 40 mM Tris-HCl (pH 8.5), 50 mM KCl, 12 mM $MgCl_2$, 10 mM DTT, 100 µg/ml BSA, 40 U of T7 RNA polymerase, 8 U of AMV reverse transcriptase, 0.2 U RNase H, 12.5 units RNAse inhibitor, 0.2 µM of each primer, 1 mM each dNTP, and 2 mM each NTP.

Because of the relatively low temperature used in 3SR, it is preferred that the annealing temperature of the primers be further optimized through the use of denaturing agents such as glycerol, di-methyl sulfoxide and polyethylene glycol (PEG), or the use of additives such as gp32 or single stranded binding protein, higher concentrations of BSA and gelatin, or the use of detergents such as Tween 20, Nonidet NP40, or Triton X-100 to ensure specificity during amplification.

iii. Primers for Amplification of *C. parvum* DNA and *G. lamblia* DNA

In a preferred embodiment, the primers used for amplification of *C. parvum* DNA and *G. lamblia* DNA are synthetic oligonucleotides that are prepared by an automated instrument (e.g, Applied Biosystems Inc., Foster City, Calif., US). Alternatively, primers are purchased from commercial suppliers such as Integrated DNA Technologies, Skokie, Ill., US.

In a preferred embodiment, the primers used for the amplification reactions amplify the HSP70 gene sequence of *C. parvum*, GenBank accession number U11761, SEQ ID NO:1. One such primer pair is SEQ ID NO:2 and SEQ ID NO:3, shown below, which amplifies DNA or RNA from many different Cryptosporidium species including *C. parvum* and which yields 307 base pair amplicons from *C. parvum* nucleic acid extracts.

SEQ ID NO:2: CTGTTGCTTA TGGTGCTGCT G

SEQ ID NO:3: CCTCTTGGTG CTGGTGGAAT A

The experimentally determined optimum annealing temperature of SEQ ID NO:2 and SEQ ID NO:3 is about 55° C.

According to a particularly preferred embodiment of the present invention, there is provided a primer pair SEQ ID NO:4 and SEQ ID NO:5, shown below, which selectively amplifies DNA or RNA from *C. parvum* but not from other Cryptosporidium species and which yields 361 base pair amplicons, corresponding to residues 2423 to 2784 of SEQ ID NO: 1, from *C. parvum* nucleic acid extracts.

SEQ ID NO:4: AAATGGTGAG CAATCCTCTG

SEQ ID NO:5: CTTGCTGCTC TTACCAGTAC

The experimentally determined optimum annealing temperature of SEQ ID NO:4 and SEQ ID NO:5 is about 55° C. Referring now to FIG. 1, there is shown a diagram of the relative map positions of primer pair SEQ ID NO:2 and SEQ ID NO:3, and the primer pair SEQ ID NO:4 and SEQ ID NO:5 within SEQ ID NO:1. Each of these two sets of primers have an internal oligonucleotide probe which is used to confirm the identity of the amplicons.

The primer pair used for selectively amplifying *C. parvum* using 3SR techniques is the same as SEQ ID NO:4 and SEQ ID NO:5 except that the reverse primer, SEQ ID NO:5, further includes the sequence AATTCTAATACGACTCAC-TATAGGGAGA at its 5'end, forming SEQ ID NO:6 as follows:

SEQ ID NO:6: AATTCTAATA CGACTCACTA TAGGGAGACT TGCTGCTCTT ACCAGTAC

This added sequence contains the necessary T7 RNA polymerase promoter and the sequences AGA and AATTC to enhance amplification using 3SR techniques.

In another embodiment of the present invention, there is provided primer pairs that selectively amplify Giardia species and which is combined with *Cryptosporidium parvum* specific pairs to produce a "multiplex" amplification reaction. Moreover, the following primers targeting the HSP gene are suitable for the detection of viable *G. lamblia* cysts in water samples (Abbaszadegan et al., 1993).

SEQ ID NO:7: AGGGCTCCGG CATAACTTTC C

SEQ ID NO:8: GTATCTGTGA CCCGTCCGAG

These primers yield 163 base pair amplicons from *G. lamblia*. The optimum annealing temperature for SEQ ID NO:7 and SEQ ID NO:8 is about 55° C.

In a preferred embodiment of the present invention, a multiplex amplification reaction is performed using the primer pair SEQ ID NO:4 and SEQ ID NO:5 (or SEQ ID NO:6), and primer pair SEQ ID NO:7 and SEQ ID NO:8 in order to simultaneously detect *C. parvum* and Giardia species.

D. Detection of Amplified DNA

After amplification, the amplified HSP target DNA is detected by any suitable method, as will be understood by those with skill in the art with reference to the disclosure herein. For example, the amplified DNA is detected by direct electrophoresis techniques using fluorescent intercalating dye or is detected by indirect techniques using hybridization probes.

i. Non-hybridization Techniques

In a preferred embodiment, the amplified polynucleotide is detected using non-hybridization techniques. First, electrophoresis through agarose is used to separate, identify, and purify amplicons produced according to the present invention. The location of DNA within the gel is then determined directly by staining with low concentrations of the fluorescent intercalating dye ethidium bromide, and bands corresponding to the predicted length for amplified target DNA are then detected by examination of the gel in ultraviolet light.

ii. Hybridization Techniques

In another preferred embodiment, the amplified polynucleotide is detected using hybridization with suitable probes. First, electrophoresis through agarose is used to separate, and identify amplicons produced according to the present invention. Then, the DNA bands from the electrophoresed gel are transferred to a membrane support by capillary action. A typical transfer protocol includes denaturing the DNA within the gel using an alkaline solution, such as 0.4 M NaOH, 0.6 M NaCl, followed by a neutralization step in a buffer solution, such as 1.5 M NaCl, 0.5 M Tris-HCl, pH 7.5. The gel is then equilibrated with a high ionic strength transfer buffer, such as 10×SSC, where 1×SSC is 0.15 M NaCl, 0.015 M Na citrate.

Amplified target DNA that has been captured on a solid support, such as nylon or nitrocellulose membrane, is detected by using a labeled hybridization probe, such as single-stranded oligonucleic acid (DNA) probe or oligo peptide nucleic acid (PNAs) probes which are sequence-complementary to a sequence located between the two selected oligonucleotide primers in the HSP70 gene or in a G. lamblia HSP gene. According to a preferred embodiment, the probes used to detect the amplified nucleic acid are peptide nucleic acids.

In a preferred embodiment, the probe is labeled with a radioactive or fluorescent tag, or attached directly or indirectly to an enzyme molecule. Then, the membrane-bound amplified target DNA is incubated with the probe under hybridization conditions. Following hybridization, excess probe is washed away. If the hybridization probe is radioactively tagged, the remaining hybridized probe is detected by autoradiography or scintillation counting. If the probe contains biotin or some other chemical group for which there are specific binding molecules, like avidin and antibodies, then the immobilized probe is detected with an enzyme attached to the specific binding molecule, such as horseradish peroxidase or alkaline phosphatase attached to streptavidin.

A preferred method of detection is via hybridization with a nonradioactive 5' digoxigenin (DIG)-labeled probe or with fluorescein isothiocyanate (FITC)-labeled probe. Following hybridization, the solid support is washed with a high ionic strength buffer, such as 5×SSC, at between about 50° C. to 70° C. The immobilized hybridization probe that remains after washing is visualized by incubating the solid support with anti-DIG antibody conjugated to alkaline phosphatase or with anti-DIG antibody, as appropriate, followed by addition of a chemiluminescent substrate, such as Lumigen-PPD (Roche Molecular Biochemicals, Ind., US). The support is finally washed, sealed in Saran Wrap®, and exposed to X-ray film to detect any chemiluminescence.

In another preferred embodiment, amplicons are hybridized to a hapten-labeled PNA probe by incubation in Tris buffer at room temperature for 10 minutes. The products of this reaction are then subjected to gel electrophoresis, transferred to a support membrane, and detected by application of anti-hapten antibodies conjugated to alkaline phosphatase or horse radish peroxidase.

According to one embodiment of the present invention, there is provided a DNA or a PNA probe which specifically hybridizes with sequences of C. parvum. SEQ ID NO:9 and SEQ ID NO:10, which hybridizes with residues 2423 to 2446 and 2475 to 2495, respectively, are exemplary of C. parvum specific probes, though SEQ ID NO:9 is the preferred probe for in-situ hybridization:

SEQ ID NO:9: AAATGGTGAG CAATCCTCTG CCG

SEQ ID NO:10: CCATTATCAC TCGGTTTAGA

However, shorter sequences which specifically hybridize with HSP70 sequences of C. parvum are also suitable, as will be understood by those with skill in the art with reference to the disclosure herein. For example, SEQ ID NO:4 and SEQ ID NO:5 can also be used is suitably labeled.

Referring again to FIG. 1, there is shown a diagram of the relative map positions of probes SEQ ID NO:9 and SEQ ID NO:10 within the HSP70 gene sequence SEQ ID NO:1. SEQ ID NO:9 will detect C. parvum specific sequences of any HSP70 targets having complementary sequences to nucleotide base numbers 2423 to 2446 of SEQ ID NO:1. Therefore, SEQ ID NO:9 will detect the amplicons of the SEQ ID NO:2 and SEQ ID NO:3 primer pair. SEQ ID NO:10 will detect C. parvum specific sequences of any HSP70 targets having complementary sequences to nucleotide base numbers 2475 to 2495 of SEQ ID NO:1. Therefore, SEQ ID NO:10 will detect the amplicons produced using primer pairs SEQ ID NO:2 and SEQ ID NO:3; and SEQ ID NO:4 and SEQ ID NO:5, among others.

Similarly, SEQ ID NO:11 will detect G. lamblia produced using primer pair SEQ ID NO:7 and SEQ ID NO:8:

SEQ ID NO:11: CAGGCCTTGG CGTTCCCGAA G

In a preferred embodiment, Giardia HSP probes are combined with probes for C. parvum HSP70 for simultaneous detection of C. parvum and G. lamblia amplicons produced in a multiplex amplification reaction.

Figure 2:
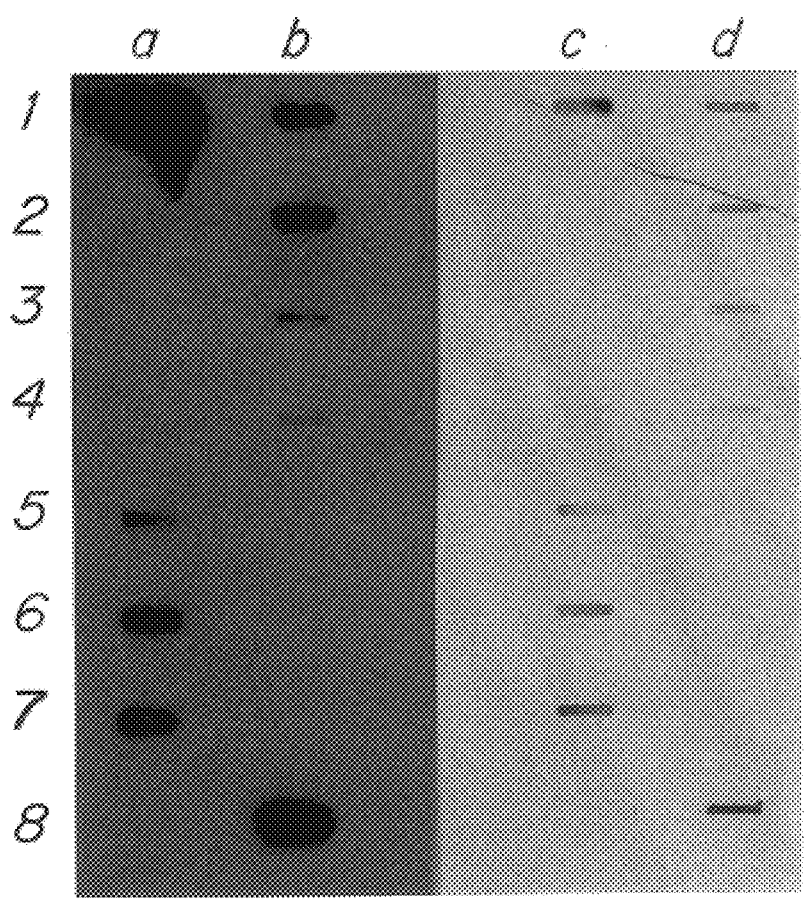
FIG. 2 shows a comparison of *C. parvum* DNA amplicon detection by DNA probe hybridization, left panel, with a *C. parvum* DNA amplicon detection by PNA probe hybridization, right panel.

Referring now to FIG. 2, there is shown a comparison of C. parvum DNA amplicon detection by DNA probe hybridization, left panel, with a C. parvum DNA amplicon detection by PNA probe hybridization, right panel. The amplicons were obtained from purified C. parvum oocysts using PCR performed with the primer pair SEQ ID NO:4 and SEQ ID NO:5 and then the reaction products were serially diluted and transferred to duplicate nylon membranes using a slot blot manifold. The amplicons were then detected by hybridization with either a 20-base digoxigenin-labeled DNA probe according to SEQ ID NO:10 followed by alkaline phosphatase mediated chemiluminescence, left panel; or a 10-base biotin-labeled PNA probe, ATCACTCGGT, residues 6–15 of SEQ ID NO:10, followed by alkaline phosphatase mediated colorimetric detection, right panel. Hybridization with the DNA probe was performed using optimized salt concentrations (0.2 M), stringent annealing temperature (59° C.), and rigorous washing protocols. Hybridization with the PNA probe was performed in a simple buffer at room temperature. The chemiluminescence utilized for the digoxigenin-labeled DNA probe in the left panel necessitated use of a darkroom whereas the colorimetric detection used for the PNA probe in the right panel was performed in full daylight on an open laboratory bench. Slots a1, b8, c1, and d8 contained unhybridized probe.

As can be seen, the PNA probes yielded essentially the same results as the digoxigenin-labeled DNA probes. However, detection with the PNA probes was faster and less complicated than detection with the DNA probes, and detection with the PNA probes did not require the dark room that detection with the DNA probes required.

Figure 3:
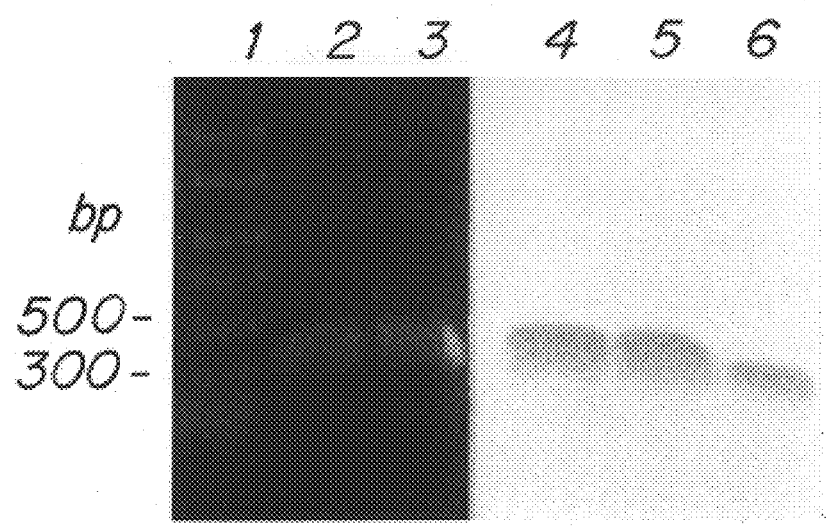
FIG. 3 shows a comparison of *C. parvum* DNA amplicon detection by gel electrophoresis and *C. parvum* DNA amplicon detection PNA probe hybridization.

Referring now to FIG. 3, there is shown a comparison of *C. parvum* DNA amplicon detection by gel electrophoresis using direct detection, lanes 2 and 3, with *C. parvum* DNA amplicon detection using indirect detection by PNA probe hybridization, lanes 4–6. In summary, 361 bp *C. parvum* specific amplicons produced by PCR using primer pair SEQ ID NO:4 and SEQ ID NO:5 were hybridized in solution for 5 minutes at room temperature with a biotin-labeled PNA probe, residues 6–15 of SEQ ID NO:10. The resulting hybrids were subjected to agarose gel electrophoresis using standard conditions. Half of the gel was stained with ethidium bromide and photographed with a polaroid camera, lanes 2 and 3, left panel. The PNA-DNA hybrids on the other part of the gel were transferred to a nylon membrane and detected directly using a streptavidin-AP conjugate, lanes 4–6, right panel. As can be seen, pre-gel hybridization using the PNA probe technique, lanes 4–6, provides the same information as the gel electrophoresis, lanes 2 and 3, but also provides confirmatory hybridization information about amplicon size.

III. DETERMINATION OF THE PRESENCE OF VIABLE *C. PARVUM* AND *G. LAMBLIA* ORGANISMS

The presence of viable *Cryptosporidium parvum* is determined by, first, recovering *C. parvum* oocysts from a sample. Next, expression of *Cryptosporidium parvum* HSP70 mRNA is induced from viable *Cryptosporidium parvum* organisms and the expressed mRNA is extracted and amplified; or the expressed mRNA is extracted, reverse transcribed into cDNA and the cDNA is amplified. Finally, the amplicons are detected using appropriate methods such as hybridization with DNA or PNA probes. In a preferred embodiment, the presence of viable *Giardia lamblia* is simultaneously determined with determining the presence of viable *Cryptosporidium parvum* using corresponding procedures to induce the expression of a *Giardia lamblia* HSP mRNA, and extracting and amplifying the expressed mRNA; or by extracting the expressed mRNA, reverse transcribing the mRNA into cDNA and amplifying the cDNA; and then detecting the amplicons.

A. Recovery of Oocysts and Cysts

The presence of viable *C. parvum*, or *C. parvum* and *G. lamblia*, is determined by, first, recovering *C. parvum* oocysts and *G. lamblia* cysts from a potentially contaminated water sample or from another appropriate sample such as a host stool sample, as disclosed above.

B. Induction of Expression of HSP mRNA

Expression of mRNA from HSP genes is induced by incubating cysts, oocysts or infected cells at about 37° C. to about 42° C. for between about 30 minutes to about 2 hours.

C. Extraction of HSP mRNA

The expressed HSP mRNA template is extracted from lysed cysts, oocysts or infected cells. This can be done by using a S.N.A.P. Kit or a Micro-FastTrack Kit (Invitrogen Corporation, Carlsbad, Calif., US) according to the manufacturer's instructions, or by other suitable techniques, as will be understood by those with skill in the art with reference to the disclosure herein.

D. Reverse Transcription of Extracted mRNA into cDNA and Amplification of the cDNA In one embodiment, the extracted mRNA is reverse transcribed into cDNA complementary to the HSP mRNA using a reverse transcriptase or a DNA polymerase having reverse transcriptase activity, sufficient amounts of four different nucleotide triphosphates, such as dATP, dCTP, dGTP, dUTP or their analogs, and a first primer. In a preferred embodiment, the first primer is SEQ ID NO:5.

After reverse transcription, the cDNA is amplified, such as by using techniques disclosed in section II.C. In a particularly preferred embodiment, the cDNA is amplified using PCR with SEQ ID NO:4 and SEQ ID NO:5 as the primers.

E. Direct Amplification of Extracted mRNA

In another embodiment, the extracted mRNA is amplified directly using suitable amplification methods rather than reverse transcribing the extracted mRNA into cDNA. In a preferred embodiment, the mRNA is amplified using an isothermal amplification reaction such as 3SR, according to techniques disclosed in section II.C. Primers SEQ ID NO:4 and SEQ ID NO:6 are suitable for amplifying HSP70 mRNA using 3SR.

F. Detection of Amplicons

After amplification, the polynucleotide amplicons are detected using techniques disclosed in section II.D. In a particularly preferred embodiment, the amplicons are detected using PNA probes as disclosed in section II.D.ii.

IV. DETERMINATION OF THE PRESENCE OF INFECTIVE *C. PARVUM* ORGANISMS

The presence of infective *C. parvum* is determined by, first, recovering *C. parvum* oocysts from a sample. The oocysts are then decontaminated and, optionally, subjected to an excystation protocol. Next, appropriate host cell monolayers are inoculated and incubated. Then, the expressed HSP70 mRNA is extracted and amplified directly; or the expressed mRNA is extracted and reverse transcribed into cDNA and the cDNA is amplified. Finally, the amplicons are detected using appropriate methods. Alternately, instead of extracting the expressed HSP70 mRNA, the presence of the expressed HSP70 mRNA can be detected in-situ by hybridization with DNA or PNA probes; or the expressed HSP70 mRNA can be amplified in-situ and the amplicons can be detected in-situ directly or indirectly. Further, infectivity can be quantified.

A. Recovery of Oocysts

The presence of infective *C. parvum* is determined by, first, recovering *C. parvum* oocysts from a potentially contaminated water sample or from another appropriate sample such as a host stool sample, as disclosed above.

B. Oocyst Decontamination and Excystation

After recovery, the oocysts are decontaminated to kill other microorganisms that can be present in the sample. One preferred method of decontamination comprises treating the recovered oocysts with 10% chlorine bleach followed by washing with sterile 0.1% sodium thiosulfate to remove residual chlorine. If necessary, oocysts can also be treated with antibiotics prior to inoculation. Alternately, Method 1622 can be used in place of decontamination.

Optionally, the decontaminated oocysts can be subjected to an excystation procedure to release sporozoites prior to infectivity. For example, the excystation procedure comprises pelleting the oocysts for 2 minutes at 5,000×g in a-microfuge, resuspending the oocysts in ice-cold 10% chlorine bleach solution, and allowing the resuspended oocysts to stand for 10 minutes on ice. The oocysts are then washed twice by successive pelleting and resuspension in sterile ice-cold saline solution.

Alternatively, the excystation procedure can comprise suspending the oocysts in phosphate buffered saline (PBS) and placing them on ice. Then, an equal volume of cold 40% Clorox bleach solution is added to the oocyst suspension and the mixture is allowed to stand on ice for about 1 minute. Next, the oocysts are washed 2–3 times in cold PBS to remove the bleach and pre-incubated in PBS for 1 hour at 37° C. An equal volume of prewarmed excystation fluid consisting of 0.25% trypsin and 0.75% taurocholic acid is added to the oocysts, and the oocysts are incubated for up to 2 hours at 37° C. on a shaker.

When excystation is complete, excysted sporozoites are recovered by filtration through a syringe filter with a pore size of about 0.2 $\mu$m. Sporozoites are washed in Hanks Balanced Salt Solution (HBSS) to remove the excystation fluid.

Alternately, oocyst decontamination and excystation is perform using immunomagnetic separation procedure according to Method 1622 and as described in Rochelle et al., Evaluation of Immunomagnetic Separation for Recovery of Infectious *Cryptosporidium parvum* Oocysts from Environmental Samples, APPLIED AND ENVIRONMENTAL MICROBIOLOGY, 841–845, February 1999.

C. Inoculation of Host Cells with Decontaminated Oocysts and Incubation of Inoculated Host Cells Next, appropriate host cell monolayers are inoculated with the recovered oocysts, and the inoculated monolayers are incubated for between about 24 and 72 hours under conditions that permit infection of cells and expression of HSP70 mRNA. Appropriate host cells for growing *C. parvum* include CaCo-2, HCT-8, and MDBK cells (ATCC Numbers HTB-37, CCL 244, and CCL-22, respectively). In a preferred embodiment, the host cells are grown as monolayers until the monolayers are between about 75–100% confluent. Inoculation of appropriate host cells is performed by first resuspending the decontaminated *C. parvum* oocysts or sporozoites in 1 ml of cell culture growth media. Then, an inoculum is placed on the confluent host cell monolayers in a volume that is sufficient to cover the monolayer. The host cells are then be incubated at 37° C. for about 2 hours in 5% $CO_2$, 95% air. Then, inoculated monolayers are washed once with a saline-antibiotics solution to remove residual toxicity and re-incubated at 37° C.

D. Extraction of HSP mRNA, Non-in-situ Amplification and Non-in-situ Detection of Amplicons In one embodiment, the expressed HSP70 mRNA is extracted and amplified; or the expressed mRNA is extracted and reverse transcribed into cDNA and the cDNA is amplified, as disclosed in sections III.B. and III.C. Finally, the amplicons are detected as disclosed in sections III.D. and III.E.

E. In-situ Amplification of Expressed HSP mRNA

In another preferred embodiment, the HSP mRNA is amplified in-situ using in-situ PCR, in-situ 3SR or another in-situ amplification method. Reagent mixtures and conditions for in-situ PCR amplification are generally the same as those for standard PCR although concentrations of $MgCl_2$ and thermostable DNA polymerase are generally higher. Cycling parameters are determined by the optimal annealing temperature of the primers and the length of the PCR amplicons, as will be understood by those with skill in the art with reference to the disclosure herein. Reaction sensitivity and specificity can be improved by using a "hot start", which prevents mis-priming and non-specific amplification. A hot start can be achieved by adding Taq polymerase only after the amplification reagents have reached 55° C. In a preferred embodiment, chemical hot start methods, such as by inclusion of dUTP and uracil-DNA glycosylase (UDG) or Taq antibodies (TaqStart™, Clontech, Palo Alto, Calif., US), both of which inhibit PCR below 50° C., are preferred for in-situ PCR due to their relative convenience. In another preferred embodiment, a hot start can be accomplished using a heat activated polymerase such as Amplitaq Gold (Perkin Elmer, Foster City, Calif. US).

In one embodiment, the slides are heated to about 80° C. and about 30 μl of preheated (80° C.) amplification cocktail is layered onto the fixed cells. A coverslip is placed on top of the reaction mixture. The edges of the cover slip are sealed with rubber cement or, alternately, self-adhesive cover slips or chambers . Reagents for in-situ PCR according to the present method include 10 mM Tris-HCl, pH 8.3; 50 mM KCl; about 2 mM to about 5 mM $MgCl_2$; about 250 μm each of dATP, dCTP, dGTP, and dUTP; about 3 μg/ml BSA; 10% glycerol; about 0.5 μM of each primer; and about 5 U to about 10 U of thermostable polymerase. Although other dTTP may be included, dUTP is a preferred reaction component because UDG can be used to prevent carryover contamination of amplification reactions and as a chemical hot start. Temperature cycling can be performed in a dedicated in-situ PCR thermal cycler, such as Geneamp® In-situ PCR System 1000 (PE Applied Biosystems, Foster City, Calif., US). The amplification cycle is repeated up to about 40 times with denaturation and extension taking place at about 94° C. for about 1 minute and 72° C. for about 2 minutes, respectively. The annealing temperature will depend on the primers used.

In another preferred embodiment, the in-situ amplification technique used to amplify the HSP mRNA is an isothermal amplification technique such as in-situ 3SR since isothermal amplification techniques do not require high temperature cycling which can damage intact cells. Therefore, advantageously, slides having the intact cells do not need to be sealed prior to amplification with isothermal amplification techniques, unlike with in-situ PCR techniques.

F. Fixation of Infected Cells Prior to Detection of Expressed mRNA or Amplicons In a preferred embodiment, the infected cells are fixed prior to detection in a manner that preserves cell morphology. The fixation procedure preferably permits the reagents for subsequent reactions to diffuse into the semi-permeabilized cell without allowing the reaction products to diffuse out of the semi-permeabilized cells.

In one preferred method of fixation, infected cell monolayers are washed in PBS at 37° C. followed by incubation in 4% paraformaldehyde (in PBS) at between about 4 to 20° C. for about 2 hours. The cells are then rinsed twice in PBS and used for in-situ detection.

In another preferred method of fixation, the slides containing the cells are treated with methanol: acetic acid (3:1) at room temperature for 5 minutes. Following acidic methanol fixation, the cells are rehydrated in graded ethanol (95%, 70%, and 50%, 2 minutes each) and treated with 200 µl proteinase K (5 µg/ml) for 15 minutes at 37° C. in a humid chamber. After the proteinase treatment, the slides are rinsed in PBS, pH 7.4 for 5 minutes at room temperature. If the cells are to be used for detecting RNA, then 200 µl of an RNase-free DNase solution (about 750 U/ml) is layered on the cells, covered with a cover slip, and incubated in a humid chamber for about two to about four hours at room temperature. Alternatively, if only DNA is to be detected, such as after in-situ amplification of the mRNA, the cells are treated in a corresponding procedure with DNase-free RNase A. Following nuclease treatment, the cells are washed with PBS and dehydrated in graded ethanol (50%, 70%, 95%, and 100% for 2 minutes each).

G. Detection of Expressed mRNA or Amplicons

In a preferred embodiment, the expressed mRNA or the amplicons produced by in-situ amplification techniques are detected by in-situ techniques after fixation. In one preferred embodiment, the expressed mRNA or the amplicons are detected directly. Direct detection of amplicons in-situ comprises incorporation of a label such as digoxigenin (DIG)-dUTP or fluorescein-dUTP into the amplicons. The label is detected using appropriate techniques, such as immunochemically using an appropriate reagent such as alkaline phosphatase- or peroxidase-conjugated anti-DIG, or using fluorescence microscopy, respectively, as will be understood by those with skill in the art with reference to the disclosure herein.

In another preferred embodiment, the expressed mRNA or the amplicons are detected by in-situ hybridization (ISH). Detection of amplicons in-situ comprises hybridization of specific non-radioactively labeled PNA or DNA probes to the expressed HSP70 mRNA or to the amplicons after PCR, 3SR or other amplification techniques. The label on the probe is then detected either by immunochemical methods or fluorescence microscopy.

In-situ hybridization techniques allow specific nucleic acid sequences to be detected in morphologically preserved tissue sections or cells and is, therefore, a particularly preferred detection technique for quantitative detection of pathogen infections in cultured cells, as disclosed below. Further, the hybridization method is preferred because it has a higher specificity than in-situ amplification.

H. Treatment of Host Cells to Quantify Infectivity

Optionally, infectivity can be quantified by inoculating the host cells with a measured dose of inoculum. Preferably, the slides containing the host cells are pre-treated with silane, collagen, BSA, laminin, fibronectin or other cell attachment factors to increase cell adherence. Oocyst preparations are serially diluted until the inoculum contains less than about 1 oocyst per cell, i.e, a multiplicity of infection (MOI) of less than one (MOI<1). Discrete infection foci are then enumerated to quantify infectivity.

Quantitative accuracy can be negatively affected if mobile sporozoites and stage I or II merozoites are able to produce secondary infection sites. Therefore, short incubation periods, such as 24 hours, can be used to reduce mobility of organisms. In a preferred embodiment, the movement of parasites is restricted to adjacent cells by the use of overlays, such as soft agarose, agar or methylcellulose.

V. KITS FOR THE DETECTION OF CRYPTOSPORIDIUM AND GIARDIA ORGANISMS

The primers and probes, used to amplify and to detect the mere presence, or presence of viable or infective C. parvum or G. lamblia organisms, can be conveniently packaged as kits. The kit comprises a suitable amount of the primers or a suitable amount of the probe, or suitable amounts of both the primers and probe. In addition, kits can contain a suitable amount of at least one standard sample, which contains a known concentration of a C. parvum or G. lamblia species, and a negative control sample free of the protozoa of interest.

The methods and kits of the present invention have many advantages over previous methods, including the speed, sensitivity, and specificity associated with amplification procedures, such as PCR. Since the methods can detect only viable and infectious forms of Cryptosporidium and Giardia, the effectiveness of disinfection procedures can be monitored. Moreover, the human pathogen, C. parvum, can be distinguished from other Cryptosporidia, such as C. muris and C. baileyi, which only infect animal hosts.

EXAMPLES

Purified preparations of C. parvum oocysts and G. lamblia cysts were obtained from two commercial laboratories, Parasitology Research Laboratories (PRL), Phoenix, Ariz., US and Waterborne, Inc., New Orleans, La., US. C. muris oocysts were provided by J. Owens (United States Environmental Protection Agency, Cincinnati, Ohio, US) and are available commercially from PRL. C. baileyi oocysts were provided by Dr. B. Blagburn (Auburn University, Auburn, Ala., US). Cysts and oocysts were supplied as purified preparations stored in antibiotic solution or as unpurified concentrates and were stored at 4° C. Cyst and oocyst densities were determined by hemocytometer counting and lower densities were obtained by serial dilution of concentrated stocks.

EXAMPLE I

Comparison of Specificity of Primer Pairs for C. Parvum and C. Muris Oocyst DNA

A comparison was made between the specificity of primers directed to different portions of the HSP70 gene, an undefined genomic region of Cryptosporidium DNA and the 18S rRNA gene, for C. parvum and C. muris, according to the present invention as follows. DNA was extracted from C. parvum and C. muris oocysts by freezing in liquid nitrogen for 2 minutes, followed by thawing at 95° C. for 5 minutes. Five µl of the freeze-thaw lysate (equivalent to about 1,000 cysts or oocysts) was added to individual PCR amplification reactions, which also contained: 10 mM Tris-HCl, pH 8.3; 50 mM KCl; 0.01% gelatin; 2.5 mM $MgCl_2$, 0.25 µM of each primer, 200 µM each of dATP, dCTP, dGTP and dUTP; and 2 U of Amplitaq® DNA polymerase (Perkin-Elmer, Foster City, Calif., US) in a 100-µL volume.

The reactions were overlaid with two drops of sterile mineral oil (Sigma Chemical Co., St. Louis, Mo., US). Hot start reactions were performed in a DNA Thermal Cycler model 480 (Perkin-Elmer) with denaturation at 94° C. for 2 minutes, followed by 40 cycles of denaturation at 94° C. for 1 minute, annealing for 1 minute at 50° C. and extension at 72° C. for 1 minute. A final extension incubation at 72° C. for 5 minutes was included followed by 5 minutes at 5° C. to stop the reactions. PCR products (15% of the amplification reaction) were detected by standard agarose gel electrophoresis and ethidium bromide staining.

Figure 4:
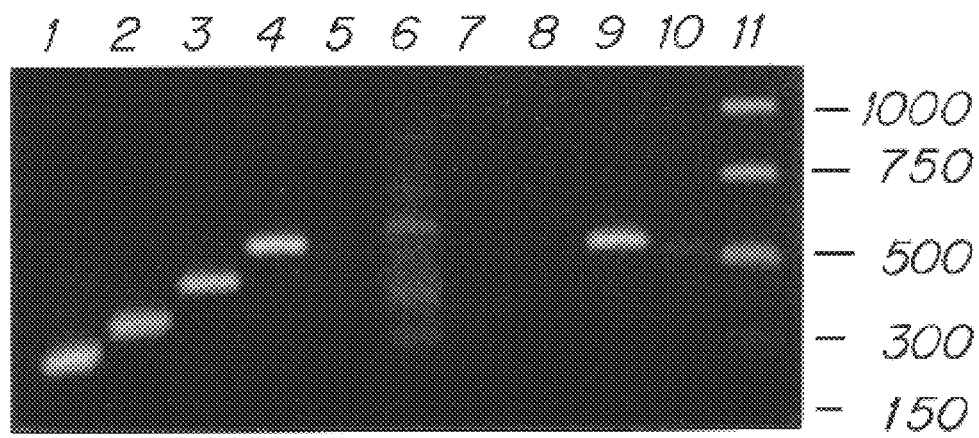
FIG. 4 shows a comparison of *C. parvum* and *C. muris* DNA amplicon detection by agarose gel electrophoresis and ethidium bromide staining using five different primer pairs.

Referring now to FIG. 4, there is shown the reaction products from the PCR amplification of DNA from *C. parvum*, lanes 1–5, and *C. muris*, lanes 6–10, using primer pair SEQ ID NO:2 and SEQ ID NO:3, primer pair SEQ ID NO:4 and SEQ ID NO:5, lanes 2 and 7, primer pair LAX469F and LAX869R, lanes 3 and 8, primer pair AWA722F and AWA1325R, lanes 4 and 9, and primer pair AWA995F and AWA1206R, lanes 5 and 10. Lane 11 contained molecular weight markers. As can be seen, primer pair SEQ ID NO:2 and SEQ ID NO:3 amplified Cryptosporidium heat shock protein gene from both species to give a 307 bp product, lanes 1 and 6. By contrast, primer pair SEQ ID NO:4 and SEQ ID NO:5 amplified the HSP70 gene from *C. parvum* to give a 361 bp product, lane 2, but not from *C. muris*, lane 7. Primer pair LAX469F and LAX869R amplifies an undefined genomic region of Cryptosporidium DNA to give a 451 bp product, lanes 3 and 8. Primer pair AWA722F and AWA1325R amplified a portion of a Cryptosporidium 18S rRNA gene to give 556 bp product, lanes 4 and 9, and primer pair AWA995F and AWA1206R amplified another portion of a Ciyptosporidium 18S rRNA gene to give a 256 bp product, lanes 5 and 10. Thus, primer pair SEQ ID NO:2 and SEQ ID NO:3 amplifies HSP70 mRNA from at least two different members of the Cryptosporidium genus, whereas primer pair SEQ ID NO:4 and SEQ ID NO:5 amplifies HSP70 mRNA from *C. parvum* only.

EXAMPLE II

Multiplex Primer Amplification of *C. Parvum* and *G. Lamblia* Followed By Detection With a *C. Parvum* Specific Probe The simultaneous amplification of target HSP polynucleotide sequences specific to *C. parvum* and to *G. lamblia* HSP polynucleotide was performed using a combination of two primer pairs in a multiplex amplification according to the present invention as follows. DNA was extracted from *C. parvum* oocysts and *G. lamblia* cysts by freezing in liquid nitrogen for 2 minutes, followed by thawing at 95° C. for 5 minutes. The PCR amplification reaction contained 10 mM Tris-HCl, pH 8.3; 50 mM KCl; 0.01% gelatin; 1.5 mM $MgCl_2$; 0.25 µM of each prime; 200 µM each of dATP, dCTP, dGTP and dUTP; and 2 U of Amplitaq® DNA polymerase (Perkin-Elmer, Foster City, Calif., US) in a 100-µL volume with 5 µL template DNA. Negative control reactions contained sterile distilled water in place of template DNA.

The reactions were overlaid with two drops of sterile mineral oil (Sigma Chemical Co., St. Louis, Mo., US). Hot start reactions were performed in a DNA Thermal Cycler model 480 (Perkin-Elmer) with denaturation at 94° C. for 2 minutes, followed by 40 cycles of denaturation at 94° C. for 1 minute, annealing for 1 minute at 52° C., and extension at 72° C. for 1 minute. A final extension incubation at 72° C. for 5 minutes was included, followed by 5 minutes at 5° C. to stop the reactions.

Figure 5:
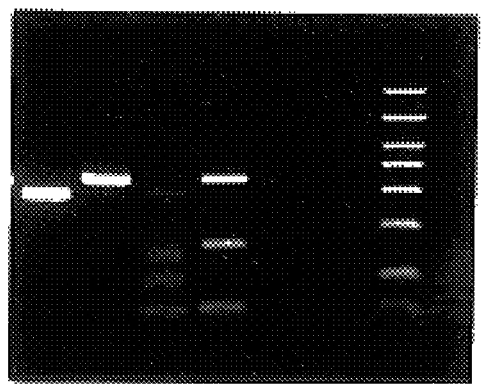
FIG. 5 shows *C. parvum* and *G. lamblia* DNA amplicon detection by agarose gel electrophoresis and ethidium bromide staining.

Referring now to FIG. 5, there is shown *C. parvum* and *G. lamblia* DNA amplicon detection by agarose gel electrophoresis and ethidium bromide staining. The amplification was performed using primer pair SEQ ID NO:2 and SEQ ID NO:3, lane 1; primer pair SEQ ID NO:4 and SEQ ID NO:5, lane 2; primer pair SEQ ID NO:2 and SEQ ID NO:3 combined with primer pair SEQ ID NO:7 and SEQ ID NO:8, lane 3; primer pair SEQ ID NO:4 and SEQ ID NO:5 combined with primer pair SEQ ID NO:7 and SEQ ID NO:8, lane 4; negative controls, lanes 5 and 6; and digoxigenin-labeled molecular weight markers, lane 7.

As can be seen, amplification reactions primed only with SEQ ID NO:2 and SEQ ID NO:3 produced the expected 307 base pair product, lane 1. Amplification reactions primed only with SEQ ID NO:4 and SEQ ID NO:5 produced the expected 361 base pair product, lane 2. Amplification reactions primed with both primer pair SEQ ID NO:2 and SEQ ID NO:3, and primer pair SEQ ID NO:7 and SEQ ID NO:8 did not produce visible products, lane 3, because this combination of primers was not suitable for multiplex PCR. Amplification reactions primed with primer pair SEQ ID NO:4 and SEQ ID NO:5, and primer pair SEQ ID NO:7 and SEQ ID NO:8, lane 4, produced both the 361 base pair product from *C. parvum* and the 163 base pair products from *G. lamblia*.

Next, a Southern blot of the gel shown in FIG. 5 was prepared as follows. The DNA was denatured by incubation of the gel for 30 minutes each in 0.4 M NaOH, 0.6 M NaCl followed by 1.5 M NaCl, 0.5 M Tris-HCl, pH 7.5 at room temperature. The gel was then incubated for 20 minutes in 10×SSC (1×SSC is 0.15 M NaCl, 0.015 M Na citrate). The denatured DNA was transferred to a positively charged nylon membrane (Roche Molecular Biochemicals, Indianapolis, Ind., US) by overnight capillary blotting in 10×SSC. The transferred DNA was cross-linked to the membrane by UV irradiation (120 mJ for 2 min) followed by drying at 80° C.

The membrane was prehybridized for 1 hour in 20 ml of hybridization solution which contained 5×SSC, 1% blocking reagent (Roche Molecular Biochemicals, Indianapolis, Ind., US), 0.1% sarcosine, 0.02% SDS at 64° C. The membrane was then hybridized in fresh hybridization solution containing 50 pmoles of 5'-fluorescein labeled oligonucleotide probe SEQ ID NO:10 for 18 hours at 64° C. in a rotary hybridization oven (Model 310, Robbins Scientific, Sunnyvale, Calif., US). Stringency washes containing 20 mM Tris-HCl, pH 7.4, 0.01% SDS, and 5×SSC were performed at 70° C., twice for 15 minutes each.

Hybridized probe was detected with an anti-fluorescein alkaline phosphatase conjugate and a chemiluminescent substrate. Membranes were washed for 5 minutes in 20 ml of 0.3% Tween 20 followed by 30 minutes incubation in 100 ml of 1% blocking reagent. Both of these solutions were made up in 0.1 M maleic acid, 0.15 M NaCl, pH 7.5 and all incubations were at 23° C. in a rotary hybridization oven. Fluorescein labeled anti-Digoxigenin (1.5 U, Roche Molecular Biochemicals, Indianapolis, Ind., US) was added in 20 ml of 0.1 M Tris-HCl, pH 7.5, 0.15 M NaCl, 1% blocking reagent and incubated for 15 minutes to label the molecular size markers. Anti-fluorescein alkaline phosphatase (1.5 U, Roche Molecular Biochemicals, Indianapolis, Ind. US) was added to the membrane in 20 ml of 0.1 M Tris-HCl, pH 7.5, 0.15 M NaCl, 1% blocking reagent and incubated for 30 minutes. The membranes were washed twice in 100 ml of 0.3% Tween 20 followed by 5 minutes in 20 ml of 0.1 M Tris, 0.1 M NaCl, 50 mM $MgCl_2$, pH 9.5 and then incubated for 15 minutes at 37° C. with Lumigen®-PPD (0.1 mg/ml; Roche Molecular Biochemicals, Indianapolis, Ind. US) in 1 ml of 0.1 M Tris, 0.1 M NaCl, 50 mM $MgCl_2$, pH 9.5. The membrane was sealed in Saran Wrap® and incubated at room temperature for 1 hour prior to exposure to X-ray film (Fuji RX, Fisher Scientific, Tustin, Calif., US) for 15 minutes.

Figure 6:
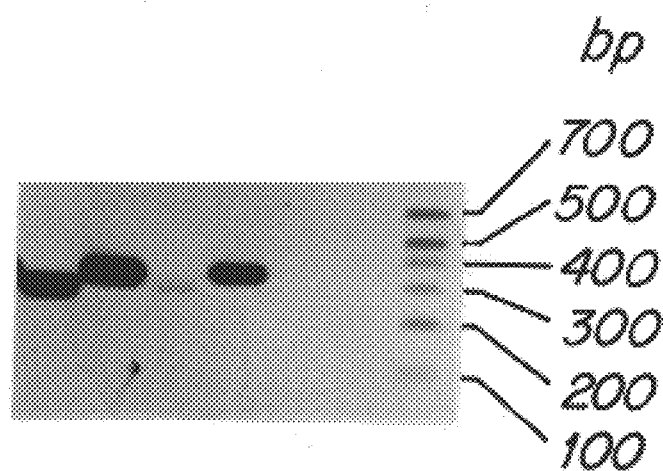
FIG. 6 shows a Southern blot of the gel shown in FIG. 5 hybridized with a DNA probe having SEQ ID NO:10 which was labeled with fluorescein and detected by a chemiluminescent reaction mediated by alkaline phosphatase conjugated anti-fluorescein antibody.

Referring now to FIG. 6, there is shown the Southern blot of the gel shown in FIG. 2 hybridized with a DNA probe having SEQ ID NO:10 which was labeled with fluorescein and detected by a chemiluminescent reaction mediated by alkaline phosphatase conjugated anti-fluorescein antibody. As can be seen, the probe specifically detected *C. parvum* amplicons that are 307 base pair, lanes 1 and 3, and 361 base pair, lanes 2 and 4, in size. However, the *C. parvum* specific probe did not hybridize with *G. lamblia* sequences from either multiplex reaction, lanes 3 and 4, showing that the *C. parvum* probe will not cross react with Giardia amplicons.

EXAMPLE III

Comparison of Specificity of Primer Pairs For Cryptosporidium DNA Followed By Detection With a *C. Parvum* Specific Probe A comparison was made between the specificity of two primer pairs used to amplify DNA extracted from a variety of Cryptosporidium species, which was followed by detection with a *C. parvum* specific probe. First, DNA was extracted from *C. parvum*, *C. muris* and *C. baileyi* oocysts by freezing in liquid nitrogen for 2 minutes, followed by thawing at 95° C. for 5 minutes. PCR amplification reactions were conducted using primer pair SEQ ID NO:2 and SEQ ID NO:3, or primer pair SEQ ID NO:4 and SEQ ID NO:5 essentially as described in Example I. The amplicons were detected by standard agarose gel electrophoresis and ethidium bromide staining.

Figure 7:
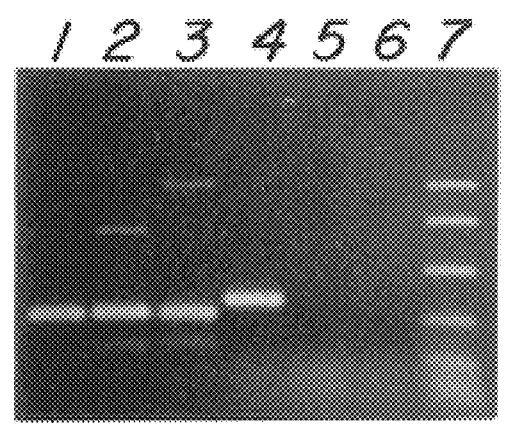
FIG. 7 shows a comparison of *C. parvum, C. muris*, and *C. baileyi* DNA amplicon detection by agarose gel electrophoresis and ethidium bromide staining using primers having SEQ ID NO:2 and SEQ ID NO:3, lanes 1–3, and primers SEQ ID NO:4 and SEQ ID NO:5, lanes 4–6.

Referring now to FIG. 7, there is shown a comparison amplicons produced with primers SEQ ID NO:2 and SEQ ID NO:3, lanes 1–3, and primers SEQ ID NO:4 and SEQ ID NO:5, lanes 4–6, from *C. parvum*, lanes 1 and 4; *C. muris*, lanes 2 and 5; *C. baileyi*, lanes 3 an 6, as detected by agarose gel electrophoresis and ethidium bromide staining. Lane 7 contained 50, 150, 300, 500, 750, 1000 base pair molecular size standards.

As can be seen in FIG. 7, primer pair SEQ ID NO:2 and SEQ ID NO:3 amplified nucleic acid sequences from all three Cryptosporidium species, lanes 1–3. In contrast, primer pair SEQ ID NO:4 and SEQ ID NO:5 only amplified DNA target sequences from *C. parvum*, lane 4, but not from *C. muris*, lane 5, or from *C. baileyi*, lane 6.

Figure 8:
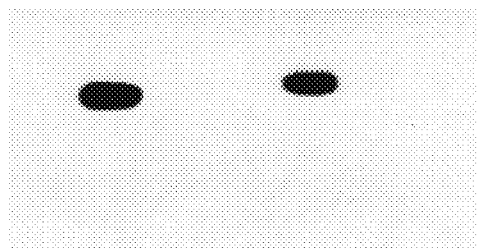
FIG. 8 shows a Southern blot of the gel shown in FIG. 7 hybridized with the SEQ ID NO:10 oligonucleotide probe, which was labeled with fluorescein and detected by chemiluminescence using an anti-fluorescein antibody conjugated to alkaline phosphatase.

Referring now to FIG. 8, there is shown a Southern blot of the gel shown in FIG. 7 hybridized with a DNA probe having SEQ ID NO:10 which was labeled with fluorescein and detected by chemiluminescence using an anti-fluorescein antibody conjugated to alkaline phosphatase, done essentially as described in Example II. As can be seen, the probe having SEQ ID NO:10 detected both *C. parvum* HSP70 amplicons, lanes 1 and 4, but did not detect the amplicons of *C. muris*, lane 2 and 5, or *C. baileyi*, lane 3 and 6, amplicons, demonstrating that the probe was specific to *C. parvum*.

EXAMPLE IV

Detection of *C. Parvum* Infected cell Cultures Using a *C. Parvum* Specific Primer Pair and Probe The combination of using a *C. parvum* specific primer pair a with the *C. parvum* specific probe to detect infected cells was demonstrated as follows. *C. parvum* oocysts were recovered from water samples and concentrated, and template DNA was extracted from infected cells and oocysts for amplification as follows. 641 L of source water (0.65 NTU) was filtered through a 1 μm nominal porosity yarn-wound polypropylene filter. The filtration flow rate was restricted to about 4 liters/minute. The filter fibers were then cut, teased and washed with a buffered detergent solution. Any oocysts or cysts that may have been eluted from the filter were concentrated by centrifugation and partially purified by flotation on a Percoll-sucrose solution with a specific gravity of 1.1. The final volume of the concentrated oocyst or cyst containing fraction was 1.3 ml. A 100 μL amount of this concentrate was seeded with 0.5–500 *C. parvum* oocysts (determined by serial dilution).

Total DNA was extracted from infected mammalian cell cultures and seeded concentrates of source water samples (100 μl) by lysis in 50 mM Tris-HCl, 20 mM EDTA, pH 8, containing 2 mg/proteinase K and 0.5% sarkosyl, followed by incubation at 37° C. for 1 h. Then, 5 M NaCl was added to give a final concentration of 1 M, and CTAB was added to a concentration of 1%. Following incubation at 65° C. for 30 minutes, the lysate was subjected to one freeze/thaw cycle and phenol/chloroform extraction. The DNA was precipitated by the addition of 0.6 vol of isopropanol, and the DNA precipitate was washed with 70% ethanol. After desiccation, the DNA pellet was resuspended in 100 μL of sterile distilled water.

The amplification reaction conditions using primer pair SEQ ID NO:4 and SEQ ID NO:5 were generally the same as in Example I. DNA was amplified by 40 cycles of denaturation at 94° C. for 45 sec, annealing for 45 sec at 55° C. and extension at 72° C. for 1 minute in containing 1.5 mM $MgCl_2$. The seeded water concentrate amplification reactions also contained 10 μg/ml BSA.

PCR products (15% of the amplification reaction) were detected by standard agarose gel electrophoresis and ethidium bromide staining. DNA transfer, hybridization and detection were performed essentially as described in Example II. The membrane was hybridized with the SEQ ID NO:10 *C. parvum* specific probe in 1×SSC at 57° C. for 18 hours and washed in 1×SSC at 54° C.

Figure 9:
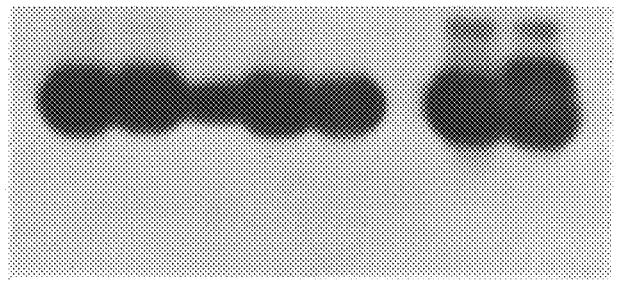
FIG. 9 shows a Southern blot of a gel hybridized a with a *C. parvum* specific probe demonstrating the detection of *C parvum* infected cells.

Referring now to FIG. 9, there is shown a Southern blot of the gel hybridized a with a DNA probe having SEQ ID NO:10 which was labeled with fluorescein and detected by a chemiluminescent reaction mediated by alkaline phosphatase conjugated anti-fluorescein antibody done essentially as described in Example II, where the DNA was extracted from five individual growth chambers containing mammalian cell cultures infected with *C. parvum*, lanes 1–5, uninfected cultured cells, lane 6, and environmental water concentrates seeded with *C. parvum*, lanes 7 and 8. As can be seen, the combination of using the primer pair SEQ ID NO:4 and SEQ ID NO:5 with the *C. parvum* specific probe having SEQ ID NO:10 gave a strong detection signal whenever *C. parvum* specific sequences were present in the DNA extracts, lanes 1–5 and lanes 7–8, while no signal was detected from uninfected cultured cells, lane 6. This demonstrates the combination of using a *C. parvum* specific primer pair a with the *C. parvum* specific probe will detect *C parvum* infected cells.

EXAMPLE V

Detection of *C. Parvum* Infected Cell Cultures Using In-situ Hybridization Techniques Amplified *C. parvum* DNA was detected using in-situ hybridization techniques according to the present invention as follows. Following inoculation with oocysts, cells were incubated for 24–72 hours. Infected cell monolayers were fixed in 4% parafornaldehyde for 2 hours, washed with PBS, and dehydrated in graded ethanol. The fixed cells were permeabilized with proteinase K (10 μg/ml in PBS for 5–30 minutes) and refixed in 4% paraformaldehyde for 20 minutes.

Next, the fixed cell monolayer was incubated in hybridization solution (0.9 M NaCl) containing 20 pmol of 5'-digoxigenin (DIG) labeled DNA probe, or 5'-biotin labeled PNA probe at 5° C. below the disassociation temperatures of the probes. The DIG or biotin labeled probes were then detected using anti-DIG or anti-biotin antibodies conjugated to alkaline phosphatase and a colorimetric substrate (nitroblue tetrazolium-bromochloro-indolyl phosphate). The alkaline phosphatase acts on the substrate to produce a purple precipitate at the site of probe hybridization. This precipitate was localized at the site of probe hybridization to infectious foci.

Figure 10:
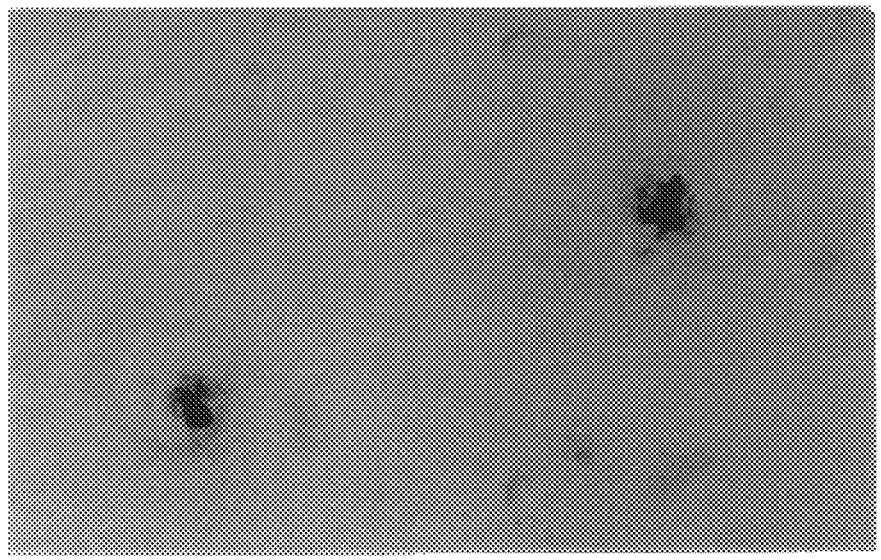
FIG. 10 shows a photomicrograph demonstrating the visualization of two infectious foci by hybridization with the DIG-labeled SEQ ID NO:10 probe.
Figure 11:
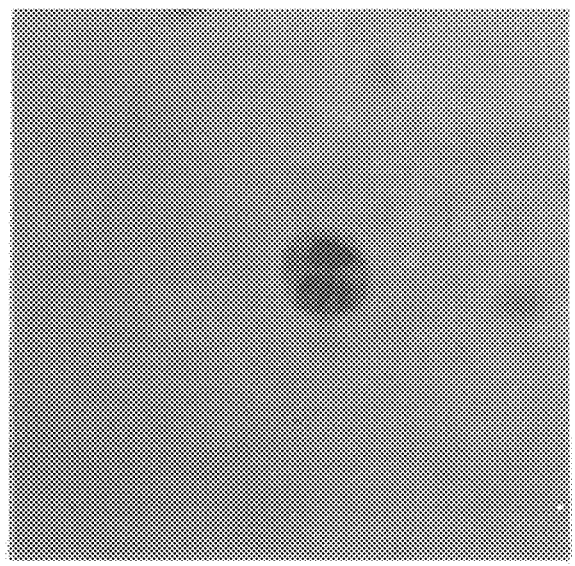
FIG. 11 shows a photomicrograph demonstrating the detection of an intact oocyst by in-situ hybridization using a DIG-labeled probe comprises the full length of the heat shock protein.

Referring now to FIG. 10, there is shown a photomicrograph demonstrating the visualization of two infectious foci by in-situ hybridization with a DIG-labeled DNA probe, SEQ ID NO:10. Referring now to FIG. 11, there is shown a photomicrograph demonstrating the detection of an intact oocyst by in-situ hybridization using a DIG-labeled DNA probe comprising the entire 361 base pair amplicon portion of SEQ ID NO:1.

All documents mentioned herein are incorporated herein by reference in their entirety. Although the present invention has been described in considerable detail with reference to certain preferred versions thereof, other versions are possible. For example, primers and probes can have additional nucleotide sequences that function as recognition sites for DNA-binding proteins, or can have linker arm or other moieties for use in solid phase or liquid hybridization systems. Therefore, the spirit and scope of the appended claims should not be limited to the description of the preferred versions described herein.

We claim:

1. A method for selectively detecting infectious *C. parvum* organisms in a sample potentially containing infectious *C. parvum* organisms and other Cryptosporidium organisms, the method comprising:
    (a) inoculating a cell culture with the sample, where the cell culture is susceptible to infection by infectious *C. parvum* organisms;
    (b) exposing the inoculated cell culture to conditions suitable to induce mRNA transcription of *C. parvum* heat shock protein 70 (HSP70) DNA;
    (c) producing a *C. parvum* HSP70 polynucleotide from at least a portion of the *C. parvum* HSP70 mRNA utilizing a first primer;
    (d) selectively amplifying the *C. parvum* HSP70 polynucleotide produced in (c); and
    (e) detecting the presence of any amplified polynucleotide formed in (c);
    where the presence of amplified polynucleotide detected in (e) indicates the presence of infectious *C. parvum* organisms in the sample.

2. The method of claim 1, where producing a *C. parvum* HSP70 polynucleotide comprises producing at least one copy of the mRNA.

3. The method of claim 1, where producing a *C. parvum* HSP70 polynucleotide comprises reverse transcribing the mRNA to produce cDNA.

4. The method of claim 1, where the portion of *C. parvum* HSP70 is that portion of SEQ ID NO:1 extending from about nucleotide 2386 to about 2784.

5. The method of claim 1, where the first primer has a sequence selected from the group consisting of SEQ ID NO:4, SEQ ID NO:5 and SEQ ID NO:6.

6. The method of claim 1, where the amplification is performed by a temperature cycling amplification reaction.

7. The method of claim 1, where the amplification is performed by an isothermal amplification reaction.

8. The method of claim 1, where the amplification is performed in-situ.

9. The method of claim 1, where the detecting is performed by subjecting the amplified polynucleotide to hybridization conditions with a DNA probe.

10. The method of claim 1, where the detecting is performed by subjecting the amplified polynucleotide to hybridization conditions with a PNA probe.

11. The method of claim 1, where the detecting is performed in-situ.

12. The method of claim 1, where the amplification is performed by an isothermal amplification reaction, and where the detecting is performed by subjecting the amplified polynucleotide to hybridization conditions with a PNA probe.

13. The method of claim 1, where the amplification is performed by an in-situ isothermal amplification reaction, and where the detecting is performed by subjecting the amplified polynucleotide to in-situ hybridization conditions with a PNA probe.

14. The method of claim 1, where the cell culture comprises a number of cells, the sample comprises a number of infective oocysts, and where the number of cells exceeds the number of infective oocysts.

15. The method of claim 5, where the amplification is performed by a polymerase chain reaction.

16. The method of claim 7, where the isothermal amplification reaction is a self-sustained sequence replication reaction.

17. The method of claim 9, where the DNA probe has a sequence selected from the group consisting of SEQ ID NO:9, SEQ ID NO:10, the complement of SEQ ID NO:9 and the complement of SEQ ID NO:10.

18. The method of claim 10, where the PNA probe has a sequence selected from the group consisting of SEQ ID NO:9, SEQ ID NO:10, the complement of SEQ ID NO:9 and the complement of SEQ ID NO:10.

19. The method of claim 12, where the isothermal amplification reaction is self-sustained sequence replication.

20. The method of claim 12, where the PNA probe has a sequence selected from the group consisting of SEQ ID NO:9, SEQ ID NO:10, the complement of SEQ ID NO:9 and the complement of SEQ ID NO:10.

21. The method of claim 13, where the isothermal amplification reaction is self-sustained sequence replication.

22. The method of claim 13, where the PNA probe has a sequence selected from the group consisting of SEQ ID NO:9, SEQ ID NO:10, the complement of SEQ ID NO:9 and the complement of SEQ ID NO:10.

23. A method for selectively detecting infectious *C. parvum* organisms in a sample potentially containing infectious *C. parvum* organisms and other Cryptosporidium organisms, the method comprising:
    (a) inoculating a cell culture with the sample, where the cell culture is susceptible to infection by infectious *C. parvum* organisms;

(b) exposing the inoculated cell culture to conditions suitable to induce mRNA transcription of *C. parvum* heat shock protein 70 (HSP70) DNA;

(c) selectively detecting the presence of transcribed mRNA; where the presence of transcribed mRNA detected in (c) indicates the presence of infectious *C. parvum* organisms in the sample.

24. The method of claim 14, where the detecting is performed by subjecting the transcribed mRNA to hybridization conditions with a DNA probe.

25. The method of claim 24, where the detecting is performed by subjecting the transcribed mRNA to hybridization conditions with a PNA probe.

26. The method of claim 23, where the detecting is performed in-situ.

27. The method of claim 23, where the cell culture comprises a number of cells, the sample comprises a number of infective oocysts, and where the number of cells exceeds the number of infective oocysts.

28. The method of claim 24, where DNA probe has a sequence selected from the group consisting of SEQ ID NO:9, SEQ ID NO:10, the complement of SEQ ID NO:9 and the complement of SEQ ID NO:10.

29. The method of claim 25, where the PNA probe has a sequence selected from the group consisting of SEQ ID NO:9, SEQ ID NO:10, the complement of SEQ ID NO:9 and the complement of SEQ ID NO:10.

* * * * *